US006867012B2

(12) United States Patent
Kishimoto et al.

(10) Patent No.: US 6,867,012 B2
(45) Date of Patent: Mar. 15, 2005

(54) DETERMINATION METHOD OF BIOLOGICAL COMPONENT AND REAGENT KIT USED THEREFOR

(75) Inventors: Takahide Kishimoto, Tsuruga (JP); Atsushi Sogabe, Tsuruga (JP); Shizuo Hattori, Tsuruga (JP); Masanori Oka, Tsuruga (JP); Yoshihisa Kawamura, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 330 days.

(21) Appl. No.: 09/998,130

(22) Filed: Dec. 3, 2001

(65) Prior Publication Data

US 2002/0119507 A1 Aug. 29, 2002

(30) Foreign Application Priority Data

Dec. 5, 2000 (JP) ...................................... 2000-370445
Mar. 29, 2001 (JP) ...................................... 2001-096724

(51) Int. Cl.[7] .............................................. C12Q 1/48
(52) U.S. Cl. ............................ 435/15; 435/26; 435/25; 435/28; 435/975
(58) Field of Search ............................ 435/15, 26, 25, 435/28, 975

(56) References Cited

U.S. PATENT DOCUMENTS 5,668,173 A * 9/1997 Garrow ....................... 514/557
5,998,191 A    12/1999 Tan et al. ..................... 435/32

FOREIGN PATENT DOCUMENTS

| EP | 0 437 373 A | 7/1991 |
|---|---|---|
| EP | 0 477 001 A | 3/1992 |
| JP | P2001-17198 A | 1/2001 |
| WO | WO 99/47559 A | 9/1999 |
| WO | WO 00/28071 A | 5/2000 |

OTHER PUBLICATIONS van Dijken et al (Archives of microbiol, V.111(1–2),pp 77–83,(Dec. 1976)(Abstract Only).*

(List continued on next page.)

*Primary Examiner*—Louise N. Leary
(74) *Attorney, Agent, or Firm*—Kenyon & Kenyon

(57) ABSTRACT

The present invention provides novel glutathione-dependent formaldehyde dehydrogenase that makes possible quantitative measurement of formaldehyde by cycling reaction, and a determination method of formaldehyde and biological components, such as creatinine, creatine, and homocysteine, which produces formaldehyde as a reaction intermediate. In addition, the present invention provides a reagent kit for the above-mentioned determination method. The present invention provides a novel determination method of a homocysteine using transferase utilizing homocysteine and other compound as a pair of substrates. Particularly, the present invention provides a determination method of homocysteine which includes bringing betaine-homocysteine methyltransferase and dimethylglycine oxidase into contact with a sample and measuring produced hydrogen peroxide or formaldehyde. Moreover, the present invention provides novel dimethylglycine oxidase stable to thiol compound, which is suitably used for the measurement. The present invention provides a reagent kit used for any of the above-mentioned determination methods of homocysteine.

73 Claims, 2 Drawing Sheets

OTHER PUBLICATIONS

Mori et al., "*Purification and Properties of Dimethylglycine Oxidase from Cylindrocarpon didymum M–1*", Agricultural and Biological Chemistry, 44(6):1383–1390 (1980).

Meskys, R. et al., "*Peculiarities of creatinline catabolism in some Arthrobacter strains*", Biologija, 1:61–64 (1997).

Kerr R. G. et al., "*An Enzyme–Based Formaldehyde Assay and Its Utility in a Sponge Sterol Biosynthetic Pathway*", J. Nat. Prod., 62(1):201–202 (1999).

Kiba N. et al., "*Determination of nano–molar levels of formaldehyde in drinking water using flow–injection system with immobilized formaldehyde dehydrogenase after off–line solid–phase extraction*", Analytica Chimica ACTA, 378(1–3):169–175 (1999).

Van Ophem P. W. et al., "*NAD–and co–substrate (GSH or factor)–dependent formaldehyde dehydrogenases from methylotrophic microorganisms act as a class III alcohol dehyrogenase*", FEMS Microbiology Letters, 116(1):87–93 (1994).

Kato N. et al., "*Formaldehyde Dehyrdogenase from Methylotrophic Yeasts*", Methods in Enzymology, 188:455–459 (1990).

M.S. Quesenberry, et al., "A Rapid Formaldehyde Assay Using Purpald Reagent: Application under Periodation Conditions", *Anal. Biochem.*, 234(1), 50–55 (1996).

*Kensa to Gijutsu*, 27(8): 973–980 (1999).

*Enzyme Handbook 9*, 1.1.1.1, "Alcohol Dehydrogenase" Springer–Verlag, pp. 1–23, (1995).

Masayoshi Yasuhara, et al., "A New Enzymatic Method to Determine Creatine", *Clin. Clim. Acta*, 122, 181–188 (1982).

O. Sugita, et al., "Reference values of serum and urine creatine, and of creatinine clearance by a new enzymatic method", *Ann. Clin. Biochem*, 29, 523–528 (1992).

Anders Andersson, et al., "Homocysteine and Other Thiols Determined in Plasma by HPLC and Thiol–Specific Post-column Derivatization", *Clin. Chem.*, 39, 1590–1597, (1993).

Lasse Uotila, et al., "A Steady–State–Kinetic Model for Formaldehyde Dehydrogenase from Human Liver", *Biochem. J.*, 177, 869–878, (1979).

Bernard Vinet, "An Enzymic Assay for the Specific Determination of Methanol in Serum", *Clin. Chem.*, 33(12), 2204–2208 (1987).

Yuzo Kayamori, et al., "A Sensitive Determination of Uric Acid in Serum Using Uricase/Catalase/Formaldehyde Dehydrogenase Coupled with Formate Dehydrogenase", *Clin. Biochem.*, 27(2), 93–97 (1994).

Yutaka Teranishi, et al., "Catalase Activities of Hydrocarbon–utilizing *Candida* Yeasts" *Agric. Biol. Chem.* 38(6), 1213–1220 (1974).

Jacob W. Dubnoff, et al., "Dimethylthetin and Dimethyl–β–Propiothetin in Methionine Synthesis", *J. Biol. Chem.*, 176, 789–796 (1948).

Raymond F. White, et al., "Betaine–Homocysteine Transmethylase in *Pseudomonas denitrificans*, a Vitamin $B_{12}$ Overproducer", *J. Bacteriol.*, 113(1), 218–223, (1973).

Timothy A. Garrow, "Purification, Kinetic Properties, and cDNA Cloning of Mammaliam Betaine–Homocysteine Methyltransferase" *J. Biol. Chem.*, 271(37), 22831–22838 (1996).

Ingo Neben, et al., "Studies on an Enzyme, S–Formylglutathione Hydrolase, of the Dissimilatory Pathway of Methanol in *Candida Boidinii*", *Biochlm. Biophys. Acta*, 614, 81–91(1980).

Horst Schütte, et al., "Purification and Properties of Formaldehyde Dehydrogenase and Formate Dehydrogenase from Candida Boidinii", *Eur. J. Biochem.* 62(1), 151–150 (1976).

\* cited by examiner

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 1
```

-continued

```
gcaattccat atgccacccg ttgggggcaa aaaggccaag                    40
```

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 2

```
atcgcggatc caggctactg tgatttgaat ttttgttttt                    40
```

DETERMINATION METHOD OF BIOLOGICAL COMPONENT AND REAGENT KIT USED THEREFOR

TECHNICAL FIELD OF THE INVENTION

The present invention relates to a convenient and highly sensitive determination method, using glutathione-dependent formaldehyde dehydrogenase, of formaldehyde or a compound forming formaldehyde as a reaction intermediate, and a reagent kit therefor. More particularly, the present invention relates to a determination method of a biological component, such as creatinine, creatine, and homocysteine and via formaldehyde as an intermediate, and a reagent kit therefor. The present invention also relates to a determination method of homocysteine using a transferase utilizing homocysteine and other substance as a pair of substrates and a reagent kit therefor.

BACKGROUND OF THE INVENTION

Formaldehyde is known to be a cytotoxin rich in reactivity with protein, membrane, and DNA, which causes various disorders by being inhaled or oral administration. Formaldehyde contained in atmosphere, waste water, and food has been considered problematic in recent years, and a convenient method for accurately measuring formaldehyde has been demanded.

As a determination method of formaldehyde, a method comprising calorimetric analysis using Hanz reagent, CTA reagent (*J. Biol. Chem.*, 231, 813 (1958)), Purpald reagent (*Anal. Biochem.*, 234(1), 50 (1996)) and an analysis method using a reagent containing phenylhydrazine, potassium ferricyanide, chloroform and methanol in combination are known. These methods are associated with problems in that they require complicated manipulation and a long time for the determination, or use of harmful reagents. As a means for solving such problems, enzymatic methods using glutathione-independent formaldehyde dehydrogenase (EC 2.1.1.46) have been disclosed (JP 5-42000 A, JP 2000-225000 A). These enzymatic methods analyze reduced nicotinamide adenine dinucleotide simultaneously produced when forming formic acid from formaldehyde, based on the enzymatic reaction or a pigment produced by the reaction of the reduced nicotinamide adenine dinucleotide. The determination sensitivity is, nevertheless, not necessarily sufficient for the measurement of a trace amount of formaldehyde, because it depends on the molar absorption coefficient of the reduced nicotinamide adenine dinucleotide or pigment.

As a highly sensitive assay of a trace amount of a substance by the use of an enzyme, a method is known wherein the determination object substrate and a coenzyme of an enzyme acting on a substrate are amplified by cycling reaction and quantitatively measured (Kensa to Gijutsu, 27(8), July, 1999). As one of the cycling methods, a determination method by an enzyme cycling method utilizing a reversible reaction using dehydrogenase and two kinds of coenzymes (thio-NAD compound and NADH compound, or NAD compound and thio-NADH compound) has been reported (JP 6-61278 B, JP 6-73477 B, JP 6-73478 B, JP 6-73479 B, JP 3023700, JP 3034969, JP 3034979, JP 3034984, JP 3034986, JP 3034987, JP 3034988, JP 8-103298 A).

JP 4-341198 A discloses a highly sensitive assay of alcohols or aldehydes using alcohol dehydrogenase and thio-NAD compound and NADH compound, or NAD compound and thio-NADH compound. The representative enzyme of the alcohol dehydrogenase used here, which catalyzes the following reaction, is the enzyme of EC1.1.1.1:

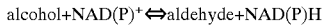

D. Schomburg, D. Stephan Eds., Enzyme Handbook 9 (Springer-Verlag) states that this enzyme oxidizes not only methanol as a substrate but also its product (formaldehyde). Since formaldehyde exists as a hydrate in an aqueous solution and as alcohol, it is a substrate oxidized with alcohol dehydrogenase allowing oxidation to acetic acid. Thus, a highly sensitive determination of formaldehyde using this enzyme is unattainable. In addition, since an aldehyde dehydrogenase, such as glutathione-independent formaldehyde dehydrogenase, irreversibly oxidizes formaldehyde, it cannot be applied to a highly sensitive determination by a cycling reaction.

In the field of analytical science, some compounds are known to be measured via formaldehyde as an intermediate. Of these, useful is the determination of creatinine, creatine and homocysteine in clinical tests.

Creatinine is a major diagnostic marker of kidney function in clinical tests, and determination of creatine is used for the analysis of disease state of muscular dystrophy, hyperthyroidism. As the determination method therefor, the Jaffe method is dominantly used, but this method is pointed out to be insufficient in the specificity. Recently, enzymatic methods using creatinine amidohydrolase, creatine amidinohydrolase, sarcosine oxidase and peroxidase having high specificity are increasingly used, but it has been pointed out that these methods may be influenced by reducing substances present in the body. There are reported some enzymatic methods wherein glutathione-independent formaldehyde dehydrogenase is used instead of peroxidase to analyze formaldehyde derived from sarcosine oxidase reaction by the above-mentioned method (*Clin. Clim. Acta*, 122, 181 (1982), *Ann. Clin. Biochem.*, 29, 523 (1992)). However, these methods are not necessarily sufficient for the measurement of a trace amount, as mentioned above.

Homocysteine is an amino acid having an SH group produced by metabolism of methionine which is an essential amino acid in the body and is generally present at a low concentration in the body. It is known that homocystinuria, which is a genetic disease of these metabolizing enzymes causing increased blood homocysteine concentrations, relates to arteriosclerosis. In recent years, the connection of homocysteine concentration of the level somewhat higher than the normal value, to cerebral infarction, myocardial infarction and depths vein thrombosis (so-called economy class syndrome) has been clarified, and the present understanding is that blood homocysteine concentration is an independent risk factor of these diseases. The standard method for determination of homocysteine has been heretofore a method using HPLC (*Clin. Chem.*, 39, 1590 (1993)), and various modifications have been also reported. The method using HPLC requires sophisticated analyzing devices and is inconvenient for processing a number of test samples. As a method without separation by HPLC, a method for determining homocysteine has been proposed to react homocysteine with S-adenosylhomocysteinase in the presence of adenosine and fluorescein-labeled S-adenosylhomocysteine, and measure S-adenosylhomocysteine present in the reaction system by fluorescence polarization immunoassay using an anti-S-adenosylhomocysteine antibody (JP 8-506478 A). Recently proposed enzymatic methods include a method comprising reacting homocysteine with homocysteine desulfrase and measuring ammonia, α-keto acid or hydrogen sulfide produced thereby (JP 2000-502262 A), a method comprising measuring hydrogen sulfide or thiol compound-substituted homocysteine produced in the presence of thiol compound, using L-methionine γ-lyase and O-acetylhomoserine-lyase capable of decomposing homocysteine (JP 2000-166597 A), a method comprising quantitatively measuring γ-substituted-α-aminobutylic acid or hydrogen sulfide derived from homocysteine by a γ-substituted-α-aminobutyrate synthase in the presence of a nucleophilic reagent substitutable with γ-mercapto group of homocysteine (JP 2000-228998 A) However, it is a general understanding that immunoassay requires a longer time and higher cost than do typical biochemical tests, and analysis methods using enzymatic reactions are not entirely satisfactory for the accurate measurement of homocysteine amount, since the blood homocysteine is in a trace amount and its concentration is about 10 μM or lower by normal value, leading to insufficient determination sensitivity, or substrate specificity of the enzyme used causes cross-reaction with substances other than homocysteine in the test sample.

As a homocysteine determination method utilizing an enzyme cycling method, a method for measuring pyruvic acid and ammonia produced by cystathionine β-synthase and cystathionine β-lyase (U.S. Pat. No. 6,174,696), a method for analyzing NAD compound or thio-NAD compound produced or consumed using homocysteine desulfrase and 2-keto-butylate dehydrogenase are known. In view of the homocysteine amount in the body, however, a method capable of assaying with higher sensitivity is desired.

It is therefore an object of the present invention to enable highly sensitive and convenient determination of formaldehyde or a compound that produces formaldehyde as a reaction intermediate. The present invention also aims at providing a method for determining homocysteine highly sensitively and conveniently without using HPLC or immunoassay.

SUMMARY OF THE INVENTION

The present inventors took note of glutathione-dependent formaldehyde dehydrogenase (EC 1.2.1.1) as an enzyme that acts reversibly on formaldehyde and succeeded in screening novel glutathione-dependent formaldehyde dehydrogenase, wherein two kinds of coenzymes can be used and the reactivity balance with the both permits progression of cycling reaction. They have then found out that formaldehyde or a compound that produces formaldehyde as a reaction intermediate of multi-step measurement, such as creatine, and creatinine, can be measured highly sensitively and conveniently by reacting this enzyme, glutathione, oxidized coenzyme and other reduced coenzyme with a sample and measuring changes in the coenzyme amount of any of them due to the enzymatic reaction.

In addition, the present inventors have found that homocysteine can be measured highly sensitively and highly accurately by reacting transferase utilizing homocysteine and other substance as a pair of substrates with a sample containing homocysteine together with the other substance and measuring the compound produced. Particularly, the present inventors have found that homocysteine can be measured highly sensitively and highly accurately by using betaine-homocysteine methyltransferase as transferase and betaine as other substrate, further decomposing the produced dimethylglycine into sarcosine, formaldehyde and hydrogen peroxide by the use of dimethylglycine oxidase, and measuring any of these compounds. According to this determination system, formaldehyde is produced as a reaction intermediate, which enables use of the above-mentioned formaldehyde dehydrogenase for the determination of homocysteine.

The present inventors have further succeeded, after screening dimethylglycine oxidase having properties suitable for use in the determination system, in isolation and purification of novel dimethylglycine oxidase resistant to thiol compound and having smaller Km value to dimethylglycine as compared to conventional enzyme. Application of this enzyme to the above-mentioned determination system led to the highly sensitive and highly accurate determination of homocysteine.

Accordingly, the present invention provides the following.

(1) A method for determining formaldehyde, which comprises bringing glutathione-dependent formaldehyde dehydrogenase having a ratio of reactivity with thio-NAD to reactivity with NAD of not less than 30%, glutathione and an oxidized coenzyme into contact with a sample, and analyzing a compound resulting from the enzymatic reaction.

(2) The method of the above-mentioned (1), wherein the ratio of reactivity with thio-NAD to reactivity with NAD of glutathione-dependent formaldehyde dehydrogenase is not less than 60%.

(3) The method of the above-mentioned (1) or (2), wherein the glutathione-dependent formaldehyde dehydrogenase has the following physico-chemical properties: action: production of S-formylglutathione and reduced coenzyme by action on formaldehyde in the presence of one oxidized coenzyme selected from the group consisting of NADs, NADPs, thio-NADs and thio-NADPs and reduced glutathione optimal pH: about 7.5–about 8.5 pH stability: about 6.0–about 9.0, and heat stability: about 40° C. or less (pH 7.5, 30 min).

(4) The method of any of the above-mentioned (1) to (3), wherein the glutathione-dependent formaldehyde dehydrogenase is derived from microorganism.

(5) The method of the above-mentioned (4), wherein the glutathione-dependent formaldehyde dehydrogenase is derived from methylotrophic yeast.

(6) The method of the above-mentioned (5), wherein the glutathione-dependent formaldehyde dehydrogenase is derived from *Hansenula* yeast.

(7) The method of the above-mentioned (6), wherein the glutathione-dependent formaldehyde dehydrogenase is derived from *Hansenula nonfermentans* IFO1473.

(8) A method for determining formaldehyde, which comprises bringing glutathione-dependent formaldehyde dehydrogenase having a ratio of reactivity with thio-NAD to reactivity with NAD of not less than 30%, glutathione, one compound selected from the group consisting of thio-NADs and thio-NADPs, and one compound selected from the group consisting of reduced NADs and reduced NADPs into contact with a sample to allow cycling reaction and analyzing changes in the amount of a compound due to the reaction.

(9) A method for determining formaldehyde, which comprises bringing glutathione-dependent formaldehyde dehydrogenase having a ratio of reactivity with thio-NAD to reactivity with NAD of not less than 30%, glutathione, one compound selected from the group consisting of reduced thio-NADs and reduced thio-NADPs, and one compound selected from the group consisting of NADs and NADPs into contact with a sample to allow cycling reaction and analyzing changes in the amount of a compound due to the reaction.

(10) The method of the above-mentioned (8), wherein the amount of the reduced thio-NADP or reduced thio-NAD compound is analyzed.

(11) The method of any of the above-mentioned (1)–(10), wherein a minimum detection limit of the formaldehyde is not more than 1 μmol/L.

(12) A method for determining a biological component, which comprises, in the determination of a biological component that produces formaldehyde as a reaction intermediate, measuring produced formaldehyde by the method of any of the above-mentioned (1)–(11).

(13) A method for determining homocysteine, which comprises bringing betaine, betaine-homocysteine methyltransferase, dimethylglycine oxidase and, where necessary, sarcosine oxidase into contact with a sample, and measuring, according to the method of any of the above-mentioned (1)–(11), formaldehyde produced by the enzymatic reactions.

(14) A method for determining creatine or creatinine, which comprises reacting creatine amidinohydrolase, sarcosine oxidase, and, where necessary, creatinine amidohydrolase and measuring, according to the method of any of the above-mentioned (1)–(11), formaldehyde produced by the enzymatic reactions.

(15) A method for determining homocysteine, which comprises bringing transferase utilizing homocysteine and other compound as a pair of substrates and said other compound into contact with a sample and measuring the resulting compound.

(16) The method of the above-mentioned (15), wherein the transferase and said other compound is a combination selected from the group consisting of betaine-homocysteine methyltransferase and betaine, betaine-homocysteine methyltransferase and dimethylthetin, homocysteine methyltransferase and S-adenosylmethionine, and N5-methyltetrahydrofolate-homocysteine methyltransferase and N5-methyltetrahydrofolate, and the resulting compound is methionine.

(17) The method of the above-mentioned (15), wherein the betaine, betaine-homocysteine methyltransferase, dimethylglycine oxidase and, where necessary, sarcosine oxidase are brought into contact with a sample, hydrogen peroxide produced by the enzymatic reactions is reacted with hydrogen donor chromogenic reagent and, where necessary, coupler, in the presence of peroxidase, and the resulting pigment is measured.

(18) The method of the above-mentioned (15), wherein the betaine, betaine-homocysteine methyltransferase, dimethylglycine oxidase and, where necessary, sarcosine oxidase are brought into contact with a sample, formaldehyde produced by the enzymatic reactions is reacted with formaldehyde dehydrogenase and oxidized coenzyme and the resulting reduced coenzyme is measured.

(19) The method of the above-mentioned (15), wherein the betaine, betaine-homocysteine methyltransferase, dimethylglycine oxidase and, where necessary, sarcosine oxidase are brought into contact with a sample, formaldehyde produced by the enzymatic reactions is reacted with glutathione, glutathione-dependent formaldehyde dehydrogenase and oxidized coenzyme and the resulting reduced coenzyme is measured.

(20) The method of any of the above-mentioned (17)–(19), wherein the dimethylglycine oxidase is an enzyme stable to thiol compound.

(21) The method of the above-mentioned (20), wherein the thiol compound is at least one kind selected from the group consisting of dithiothreitol, dithioerythritol, 2-mercaptoethanol, 2-mercaptoethanesulfonate, 2-mercaptoethylamine, cysteine, homocysteine, N-acetylcysteine, thioglycerol, thioglycolic acid, reduced glutathione and salts thereof.

(22) The method of the above-mentioned (21), wherein the thiol compound is dithiothreitol.

(23) The method of any of the above-mentioned (20)-(22), wherein the dimethylglycine oxidase shows an enzyme activity retained at least by 50% in the presence of 0.05 mmol/L dithiothreitol relative to the enzyme activity in the absence of dithiothreitol.

(24) The method of any of the above-mentioned (20)–(23), wherein the dimethylglycine oxidase is an enzyme having the following physico-chemical properties: action: acting on dimethylglycine in the presence of oxygen to produce sarcosine, formaldehyde and hydrogen peroxide, and Km value for dimethylglycine: not more than 15 mM.

(25) The method of any of the above-mentioned (20)–(24), wherein the dimethylglycine oxidase is derived from a microorganism.

(26) The method of the above-mentioned (25), wherein the dimethylglycine oxidase is derived from a microorganism belonging to the genus *Arthrobacter* or the genus *Streptomyces*.

(27) The method of the above-mentioned (26), wherein the dimethylglycine oxidase is derived from *Arthrobacter nicotianae* IFO14234 or *Streptomyces mutabilis* IFO12800.

(28) The method of any of the above-mentioned (20)–(27), wherein a minimum detection limit of the homocysteine is not more than 1 μmol/L.

(29) Glutathione-dependent formaldehyde dehydrogenase having the following physico-chemical properties: action: acting on formaldehyde in the presence of one coenzyme selected from the group consisting of NADs, NADPs, thio-NADs and thio-NADPs, reduced glutathione to produce S-formylglutathione, a reduced coenzyme, a ratio of reactivity with thio-NAD to reactivity with NAD: not less than 30%, optimal pH: about 7.5–about 8.5, pH stability: about 6.0–about 9.0, and heat stability: about 40° C. or less (pH 7.5, 30 min)

(30) The glutathione-dependent formaldehyde dehydrogenase of the above-mentioned (29), which is derived from a microorganism.

(31) The glutathione-dependent formaldehyde dehydrogenase of the above-mentioned (30), which is derived from methylotrophic yeast.

(32) The glutathione-dependent formaldehyde dehydrogenase of the above-mentioned (31), which is derived from *Hansenula* yeast.

(33) The glutathione-dependent formaldehyde dehydrogenase of the above-mentioned (32), which is derived from *Hansenula nonfermentans* IFO1473.

(34) Dimethylglycine oxidase having the following physico-chemical properties:
action: acting on dimethylglycine in the presence of oxygen to produce sarcosine, formaldehyde and hydrogen peroxide, an enzyme activity is retained at least by 50% in the presence of 0.05 mmol/L dithiothreitol relative to the enzyme activity in the absence of dithiothreitol, and Km value for dimethylglycine: not more than 15 mM.

(35) The dimethylglycine oxidase of the above-mentioned (34), which is derived from a microorganism.

(36) The dimethylglycine oxidase of the above-mentioned (35), which is derived from a microorganism belonging to the genus *Arthrobacter* or the genus *Streptomyces*.

(37) The dimethylglycine oxidase of the above-mentioned (36), which is derived from *Arthrobacter nicotianae* IFO14234, or *Streptomyces* mutabilis IFO12800.
(38) A reagent kit for formaldehyde determination, which comprises at least buffer, glutathione, glutathione-dependent formaldehyde dehydrogenase having a ratio of reactivity with thio-NAD to reactivity with NAD of not less than 30% and a reagent for analyzing a compound produced by the enzymatic reaction.
(39) The reagent kit for formaldehyde determination of the above-mentioned (38), wherein glutathione-dependent formaldehyde dehydrogenase is an enzyme of any of the above-mentioned (29)–(33).
(40) A reagent kit for formaldehyde determination, which comprises at least buffer, glutathione, glutathione-dependent formaldehyde dehydrogenase having a ratio of reactivity with thio-NAD to reactivity with NAD of not less than 30%, one compound selected from the group consisting of thio-NADs and thio-NADPs, and one compound selected from the group consisting of reduced NADs and reduced NADPs.
(41) The reagent kit for formaldehyde determination of the above-mentioned (40), wherein the glutathione-dependent formaldehyde dehydrogenase is an enzyme of any of the above-mentioned (29)–(33).
(42) A reagent kit for formaldehyde determination, which comprises at least buffer, glutathione, glutathione-dependent formaldehyde dehydrogenase having a ratio of reactivity with thio-NAD to reactivity with NAD of not less than 30%, one compound selected from the group consisting of reduced thio-NADs and reduced thio-NADPs, and one compound selected from the group consisting of NADs and NADPs.
(43) The reagent kit for formaldehyde determination of the above-mentioned (42), wherein the glutathione-dependent formaldehyde dehydrogenase is an enzyme of any of the above-mentioned (29)–(33).
(44) A reagent kit for homocysteine determination, which comprises, in addition to the reagent of any of the above-mentioned (38)–(43), betaine, betaine-homocysteine methyltransferase, dimethylglycine oxidase and, where necessary, sarcosine oxidase.
(45) A reagent kit for creatinine or creatine determination, which comprises, in addition to the reagent of any of the above-mentioned (38)–(43), creatine amidinohydrolase, sarcosine oxidase and, where necessary, creatinine amidohydrolase.
(46) A reagent kit for homocysteine determination, which comprises at least buffer, transferase utilizing homocysteine and other compound as a pair of substrates, said other compound, and a reagent for analyzing a compound produced by the enzymatic reaction.
(47) The reagent kit for homocysteine determination of the above-mentioned (46), wherein the transferase and said other compound are a combination selected from the group consisting of betaine-homocysteine methyltransferase and betaine, betaine-homocysteine methyltransferase and dimethylthetin, homocysteine methyltransferase and S-adenosylmethionine and N5-methyltetrahydrofolate-homocysteine methyltransferase and N5-methyltetrahydrofolate, and the produced compound is methionine.
(48) A reagent kit for homocysteine determination, which comprises buffer, betaine, betaine-homocysteine methyltransferase, dimethylglycine oxidase and, where necessary, sarcosine oxidase, and a reagent for measuring hydrogen peroxide produced by the enzymatic reactions.
(49) The reagent kit of the above-mentioned (48), wherein the reagent for measuring hydrogen peroxide comprises peroxidase, hydrogen donor chromogenic reagent and, where necessary, coupler.
(50) A reagent kit for homocysteine determination, which comprises betaine, betaine-homocysteine methyltransferase, dimethylglycine oxidase and, where necessary, sarcosine oxidase, and a reagent for determination of formaldehyde produced by the enzymatic reactions.
(51) The reagent kit of the above-mentioned (50), which comprises formaldehyde dehydrogenase and oxidized coenzyme as reagents for determination of the formaldehyde.
(52) The reagent kit of the above-mentioned (50), which comprises glutathione, glutathione-dependent formaldehyde dehydrogenase and oxidized coenzyme as reagents for determination of the formaldehyde.
(53) The reagent kit of any of the above-mentioned (48)–(52) for homocysteine determination, wherein the dimethylglycine oxidase is for the enzyme of any of the above-mentioned (34)–(37).

DETAILED DESCRIPTION OF THE INVENTION

Figure 1:
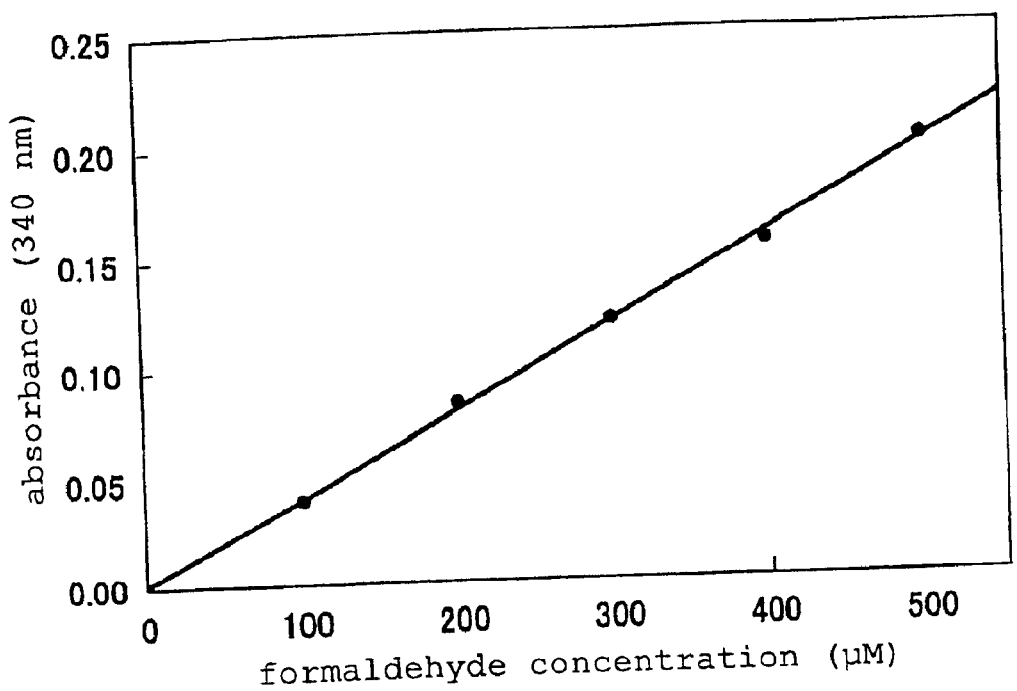
FIG. 1 shows the relationship between absorbance and formaldehyde concentration in Example 4.

The determination method of formaldehyde of the present invention is characterized in that novel glutathione-dependent formaldehyde dehydrogenase capable of utilizing two kinds of coenzymes of thio-NADs or thio-NADPs, and NADs or NADPs and having higher ratio of reactivity with thio-NAD to reactivity with NAD when compared to those known in the art is reacted with a sample together with glutathione and any of the above-mentioned oxidized coenzymes, and the amount of the compound produced or consumed is measured.

To be exact, the glutathione-dependent formaldehyde dehydrogenase (EC 1.2.1.1) used in the present invention is an enzyme reversibly catalyzes the production of S-formylglutathione and reduced coenzyme in the presence of oxidized coenzyme, using, as a substrate, S-hydroxylmethylglutathione non-enzymatically produced from glutathione and formaldehyde.

According to the present invention, glutathione-dependent formaldehyde dehydrogenase can use, as a coenzyme, thio-NADs or thio-NADPs, and NADs or NADPs. Examples of NADs include nicotineamide adenine dinucleotide, acetylpyridine adenine dinucleotide, acetylpyridine adeninehypoxanthine dinucleotide, nicotineamide hypoxanthine dinucleotide, and examples of NADPs include nicotineamide adenine dinucleotide phosphate, acetylpyridine adenine dinucleotide phosphate, acetylpyridine adeninehypoxanthine dinucleotide phosphate, and nicotineamide hypoxanthine dinucleotide phosphate. Examples of thio-NADs include thionicotineamide adenine dinucleotide, thionicotineamide hypoxanthine dinucleotide, and examples of thio-NADPs include thionicotineamide adenine dinucleotide phosphate, and thionicotineamide hypoxanthine dinucleotide phosphate.

In a preferable embodiment, the determination method of formaldehyde of the present invention is characterized in that glutathione, glutathione-dependent formaldehyde dehydrogenase, one compound selected from the group consisting of thio-NADs and thio-NADPs, and one compound selected from the group consisting of reduced NADs and reduced NADPs are reacted on a sample to allow cycling reaction, and the amount of the compound after change due to the reaction is analyzed.

In another preferable embodiment, the determination method of formaldehyde of the present invention is characterized in that glutathione, glutathione-dependent formaldehyde dehydrogenase, one compound selected from the group consisting of reduced thio-NADs and reduced thio-NADPs, and one compound selected from the group consisting of one compound selected from the group consisting of NADs and NADPs are reacted on a sample to allow cycling reaction, and the amount of the compound after change due to the reaction is analyzed.

In this cycling reaction, reduced coenzyme is produced from oxidized coenzyme, or oxidized coenzyme is produced from reduced coenzyme in proportion to the reaction time and upon amplification relative to the amount of a substrate. When the coenzyme is NAD compound or NADP compound, the absorbance around 340 nm and when it is thio-NAD compound or thio-NADP compound, the absorbance around 400 nm are measured for highly sensitive quantitative measurement of formaldehyde. The glutathione-dependent formaldehyde dehydrogenase to be used for the cycling reaction desirably contains no contaminant enzyme that decomposes formaldehyde to release same outside the cycling system, such as S-formylglutathione hydrolase, or contains said enzyme in a trace amount uninfluenceable on the measures. It is also desirable that NAD(P) degrading enzyme is not contained or contained in a trace amount uninfluenceable on the measures.

For efficient cycling reaction, glutathione-dependent formaldehyde dehydrogenase to be used in the present invention should have sufficient reactivity with thio-NADs or thio-NADPs. The ratio of reactivity with thio-NAD to reactivity with NAD is not less than 30%, preferably not less than 60%. When thio-NAD(P) compound is used as an oxidized coenzyme, in a reverse reaction, glutathione-dependent formaldehyde dehydrogenase shows sufficiently higher reactivity with reduced NAD(P) compound added than the reactivity with reduced thio-NAD(P) compound produced by forward reaction. On the other hand, when NAD(P) compound is used as an oxidized coenzyme, in a reverse reaction, glutathione-dependent formaldehyde dehydrogenase shows sufficiently higher reactivity with reduced thio-NAD(P) compound added than the reactivity with reduced NAD(P) compound produced by forward reaction. Glutathione-dependent formaldehyde dehydrogenase is known to exist in a vast range of from higher animals to microorganisms, and as an enzyme having relatively high reactivity with thio-NAD, one derived from human liver, has been reported (*Biochem. J.*, 177, 869–878 (1979)). However, glutathione-dependent formaldehyde dehydrogenase of a higher animal generally shows lower specific activity as compared to enzyme derived from microorganism, and there is no report on successful cycling reaction using this enzyme.

Therefore, the present invention provides a novel glutathione-dependent formaldehyde dehydrogenase that satisfies any of the above-mentioned conditions and is capable of catalyzing the cycling reaction. Preferably, this enzyme further has the following physico-chemical properties.

(a) action: acting on formaldehyde in the presence of one coenzyme selected from the group consisting of NADs, NADPs, thio-NADs and thio-NADPs, and reduced glutathione to produce S-formylglutathione and reduced coenzyme.

(b) optimal pH: about 7.5–about 8.5

(c) pH stability: about 6.0–about 9.0 (pH range affording the residual activity of not less than 80% after treatment at 25° C. for 24 hr.

(d) heat stability: about 40° C. or less (temperature range affording the residual activity of not less than 90% after treatment at pH 7.5 for 30 min).

The glutathione-dependent formaldehyde dehydrogenase of the present invention is free of any particular limitation on its derivation as long as it satisfies the above-mentioned conditions necessary for catalyzing the cycling reaction. Preferably, it is derived from a microorganism, more preferably derived from methylotrophic yeast, most preferably derived from *Hansenula* yeast, particularly derived from *Hansenula nonfermentans* strain IFO1473. The strain IFO1473 is available from the Institute for Fermentation, Osaka (IFO) (17-85, Juso-honmachi, 2-chome, Yodogawa-ku, Osaka 532-8686 Japan).

The glutathione-dependent formaldehyde dehydrogenase of the present invention may be genetically engineered to improve enzymatic properties such as specific activity and stability, when retaining a balance of the reactivity with two kinds of coenzymes, which is necessary for catalyzing the cycling reaction, by inducing at random or site-specific mutation.

The glutathione-dependent formaldehyde dehydrogenase of the present invention can be obtained by isolation and purification of, as a material, a cell or tissue culture producing the enzyme, or by isolating a gene encoding the enzyme protein and allowing expression thereof in a suitable host according to genetic recombination techniques. Preferable embodiment of the former is the following method.

Any of the above-mentioned glutathione-dependent formaldehyde dehydrogenase-producing microorganisms, such as *Hansenula nonfermentans* strain IFO1473, is cultured in a nutrient medium. The nutrient medium to be used may be a synthetic medium or a natural medium that contains carbon source, nitrogen source, mineral and other necessary nutrients in suitable amounts that the strain to be used can utilize. As the carbon source, for example, malic acid, and succinic acid can be used. As the nitrogen source, for example, nitrogen-containing natural products such as peptones, beef extract, and yeast extract, and inorganic nitrogen-containing compounds such as ammonium chloride, and ammonium citrate can be used. As the mineral, for example, potassium phosphate, sodium phosphate, and magnesium sulfate can be used.

The culture is generally shaking culture or aeration-agitation culture. The culture temperature is about 20–about 40° C., preferably about 25–about 37° C., and the culture pH is about 5–about 9, preferably controlled to about 6–about 8. As long as the strain in use can grow, other conditions may be employed. The culture period is generally about 1–about 7 days, glutathione-dependent formaldehyde dehydrogenase is generally produced and accumulated in the cell.

The glutathione-dependent formaldehyde dehydrogenase of the present invention can be purified by a purification method generally used. For example, after recovery of the cells, disruption by ultrasonication, mechanical disruption with glass beads, disruption with French Press, and lysis with surfactant are applied to extract intracellular fractions. The obtained extract is subjected to salting out with ammonium sulfate, sodium sulfate, metal aggregation with magnesium chloride, calcium chloride, aggregation with protamin, polyethyleneimine, ion-exchange chromatography with DEAE (diethylaminoethyl)-sepharose, CM (carboxymethyl)-sepharose, to purify glutathione-dependent formaldehyde dehydrogenase.

The determination method of formaldehyde of the present invention using a cycling reaction of the glutathione-dependent formaldehyde dehydrogenase is described in detail by referring to an example wherein thio-NAD(P) compound is used as an oxidized coenzyme. When reduced glutathione, glutathione-dependent formaldehyde dehydrogenase, oxidized thio-NAD(P) compound and reduced NAD(P) compound are brought into contact with a sample, S-formylglutathione and reduced thio-NAD(P) compound are produced from formaldehyde, reduced glutathione and oxidized thio-NAD(P) compound contained in the sample. Then, glutathione-dependent formaldehyde dehydrogenase uses an excess reduced NAD(P) compound as a coenzyme to convert the produced S-formylglutathione to formaldehyde and glutathione. Thereafter, forward reaction using oxidized thio-NAD(P) compound as a coenzyme and reverse reaction using reduced NAD(P) compound as a coenzyme are repeated, as a result of which a number of molecules of reduced thio-NAD(P) compound is produced relative to 1 molecule of formaldehyde. On the other hand, reduced NAD(P) compound is consumed as the reaction cycle proceeds. Therefore, low concentration formaldehyde can be detected with high sensitivity by monitoring increase in reduced thio-NAD(P) compound or decrease in reduced NAD(P) compound, based on the above-mentioned absorbance as an index.

In the above-mentioned determination system, when other enzyme that can use NAD(P)s as a coenzyme, but substantially cannot use thio-NAD(P)s as a coenzyme, and a substrate of this enzyme are further added, oxidized NAD(P) compound can be reproduced as a reduced form. In this case, formaldehyde is measured using increase in the reduced thio-NAD(P) compound as an index. The combination of the other enzyme and a substrate thereof that can be used for such determination system when NADs can be used is, for example, malate dehydrogenase (EC 1.1.1.37) (e.g., derived from porcine or bovine cardiac muscle) and L-malic acid, glycerol-3-phosophate dehydrogenase (EC 1.1.1.8) (e.g., derived from rabbit muscle) and L-glycerol-3-phosphate, glyceraldehyde-phosphate dehydrogenase (EC 1.1.1.12) (e.g., derived from rabbit skeletal muscle or liver, yeast or $E.$ $coli$) and D-glyseraldehyde phosphate and phosphoric acid, glucose-6-phosphate dehydrogenase (EC 1.1.1.49) (e.g., derived from Leuconostoc bacteria) and glucose-6-phosphate, glucose dehydrogenase (EC 1.1.1.47) (e.g., derived from Bacillus bacteria, Pseudomonas bacteria) and β-D-glucose, glutamate dehydrogenase (EC 1.4.1.3) (e.g., derived from bovine liver) and L-glutamic acid, and such combination when NADPs can be used is, for example, glyoxylate dehydrogenase (EC 1.2.1.17) (e.g., derived from $Pseudomonas$ $oxalaticus$) and CoA and glyoxylic acid, phosphogluconate dehydrogenase (EC 1.1.1.44) (e.g., derived from rat liver, brewer's yeast or $E.$ $coli$) and 6-phospho-D-gluconic acid, glyceraldehyde-phosphate dehydrogenase (EC 1.1.1.13) (e.g., derived from plant chloroplast) and D-glyceraldehyde-3-phosphate and phosphoric acid, glucose-6-phosphate dehydrogenase (EC 1.1.1.49) (e.g., derived from yeast or Leuconostoc bacteria) and glucose-6-phosphate, glucose dehydrogenase (EC 1.1.1.47) (e.g., derived from $Bacillus$ bacteria, $Pseudomonas$ bacteria) and β-D-glucose, glutamate dehydrogenase (EC 1.4.1.3) (e.g., derived from bovine liver) and L-glutamic acid.

The determination of formaldehyde using the glutathione-dependent formaldehyde dehydrogenase of the present invention can be also carried out without a cycling reaction as follows.

That is, glutathione, glutathione-dependent formaldehyde dehydrogenase and one coenzyme selected from the group consisting of thio-NADs, thio-NADPs, NADs and NADPs are brought into contact with a sample, and produced S-formylglutathione is measured using absorbance of UV region as an index for the determination of formaldehyde. Alternatively, S-formylglutathione hydrolase (EC 3.1.1.12) is further reacted and the produced formic acid is decomposed to carbon dioxide by formate dehydrogenase (EC1.2.1.2; EC 1.2.1.43), and the produced reduced coenzyme is measured for the determination of formaldehyde.

S-Formylglutathione hydrolase is known to be present in animal organs, methylotrophic yeast, and bacteria, and can be obtained from these sources and used. Formate dehydrogenase is an enzyme present in plant seed, methylotrophic yeast, and bacteria and can be obtained from these sources and used. Commercially available enzymes (e.g., FORMATE DEHYDROGENASE (Sigma) ) may be used.

The reduced coenzyme (NADH or NADPH compound) produced by the above-mentioned series of enzymatic reactions can be analyzed by measuring absorbance in the UV region or fluorescence. The reduced coenzyme can be also measured by measuring formazan pigment produced when reducing tetrazolium salt in the presence of an electron carrier such as diaphorase and methylphenazinium methylsulfate.

The use of glutathione-dependent formaldehyde dehydrogenase of the present invention enables detection of a trace amount of formaldehyde contained in a sample at a concentration of not more than 1 $\mu$mol/L.

The determination method of formaldehyde of the present invention is preferably used as a final step of the determination of various biological components, wherein formaldehyde is produced as a reaction intermediate for multi-step measurement.

For example, the determination of creatinine or creatine comprises reacting creatine amidinohydrolase, sarcosine oxidase and, where necessary, creatinine amidohydrolase with a sample to decompose creatinine or creatine into glycine, formaldehyde and hydrogen peroxide, and measuring hydrogen peroxide produced using color developing substrate. Thus, the glutathione-dependent formaldehyde dehydrogenase of the present invention can be used instead of a reagent for quantitative measurement of hydrogen peroxide for the determination of formaldehyde, thereby to measure creatinine or creatine. Therefore, the present invention also provides a determination method of creatinine or creatine, which method comprising bringing creatine amidinohydrolase, sarcosine oxidase and, where necessary, creatinine amidohydrolase into contact with a sample to produce formaldehyde, bringing glutathione-dependent formaldehyde dehydrogenase of the present invention, glutathione, and one oxidized coenzyme selected from the group consisting of thio-NADs, thio-NADPs, NADs and NADPs, and, where necessary, a reduced coenzyme of a different kind from the oxidized coenzyme into contact with the sample, and measuring the produced or consumed compound.

The creatine amidinohydrolase, sarcosine oxidase and creatinine amidohydrolase to be used are not particularly limited, and can be obtained from the microorganism that produce these enzymes by conventional methods or obtained from commercial sources.

As described in detail in the following, since formaldehyde can be produced by reacting betaine, betaine-homocysteine methyltransferase and dimethylglycine oxidase with a sample containing homocysteine, by the determination of formaldehyde using the glutathione-dependent formaldehyde dehydrogenase of the present invention, homocysteine can be measured. Wen sarcosine oxidase is reacted with sarcosine produced by dimethylglycine oxidase, a 2-fold amount of formaldehyde can be produced, thereby increasing the detection sensitivity.

As a different measurement object that produces formaldehyde as a reaction intermediate, for example, methanol, and uric acid are exemplified (Clin. Chem., 33/12, 2204–2208 (1987), Clin. Biochem., 27/2, 93–97 (1994)). That is, methanol produces formaldehyde and hydrogen peroxide due to alcohol oxidase (EC 1.1.3.13). Because uric acid produces formaldehyde by reacting hydrogen peroxide produced by the reaction of uricase (EC 1.7.3.3) with catalase (EC 1.11.1.6) in the presence of methanol, the above-mentioned determination method can be used to analyze formaldehyde.

The present invention also provides a reagent kit to be used for the determination method of the above-mentioned formaldehyde. The reagent kit for formaldehyde determination of the present invention contains at least buffer, glutathione, glutathione-dependent formaldehyde dehydrogenase and a reagent for analyzing the compound produced by the enzymatic reaction. Glutathione-dependent formaldehyde dehydrogenase is exemplified by those mentioned above, but is not particularly limited.

A different embodiment of the reagent kit for formaldehyde determination of the present invention contains at least buffer, glutathione, glutathione-dependent formaldehyde dehydrogenase, one compound selected from the group consisting of thio-NADs and thio-NADPs, and one compound selected from the group consisting of reduced NADs and reduced NADPs.

In another embodiment, it contains at least buffer, glutathione, glutathione-dependent formaldehyde dehydrogenase, one compound selected from the group consisting of reduced thio-NADs and reduced thio-NADPs, and one compound selected from the group consisting of NADs and NADPs. As the NADs, NADPs, thio-NADs and thio-NADPs, those mentioned above can be used.

The buffer to be used for the reagent kit of the present invention is exemplified by Tris-HCl buffer, phosphate buffer, borate buffer, and GOOD buffer. While Tris-HCl buffer and phosphate buffer are easily show changes in pH due to concentration and temperature, but advantageously economical. On the other hand, GOOD buffer is exemplified by MES, Bis-Tris, ADA, PIPES, ACES, BES, MOPS, TES, HEPES, Tricine, Bicine, POPSO, TAPS, CHES, and CAPS, and are widely used as clinical diagnostic. The kinds, concentration and pH of these buffers may be one kind or plural kinds according to the object such as preservation and enzymatic reaction of each reagent component. Any of these buffers may be preferably used at a pH during enzymatic reaction within the range of 5.0–10.0.

The reagent constituting the reagent kit of the resent invention may contain metal salt, protein, amino acid, saccharide, and an organic acid as a stabilizer. As the metal salt, salts of sodium, potassium, magnesium, calcium, iron, copper, zinc, and manganese are exemplified. As the protein, those uninfluenceable on the enzymatic reaction are desirable, such as bovine serum albumin, ovalbumin, and gelatin. Examples of the amino acid include glycine, lysine, glutamic acid, glycylglycine, and polylysine. Examples of the saccharide include monosaccharide, disaccharide, oligosaccharide, polysaccharide and their derivatives. Examples thereof include glucose, fructose, galactose, mannose, xylose, lactose, sucrose, maltose, trehalose, maltotriose, maltotetraose, maltosylcyclodextrin, α-cyclodextrin, β-cyclodextrin, γ-cyclodextrin, dextrin, amylose, glycogen, starch, inulin, glucosamine, inositol, mannitol, sorbitol, ribitol, and deoxyglucose. Examples of the organic acid include α-keto-glutaric acid, malic acid, fumaric acid, gluconic acid, cholic acid, and desoxycholic acid. In addition, boric acid, borax, sodium chloride, potassium chloride, ammonium sulfate, glycerol, and Ficoll can be used.

The reagent constituting the reagent kit of the present invention may contain antiseptic and surfactant as long as they do not adversely affect the reagent properties. Examples of the antiseptic include sodium azide, chelating agent, various antibiotics, antibacterial agent, and an antifugal agent. Specifically, sodium azide, EDTA and its salt (inclusive of metal chelate), chelating agents such as CyDTA, GHEG, DPTA-OH, DTPA, EDDA, EDDP, EDDPO, EDTA-OH, EDTPO, EGTA, HBED, HDTA, HIDA, IDA, Methyl-EDTA, NTA, NTP, NTPO, TTHA (these are commercially available from Dojindo), BND, CAA, HPO, IZU, MIT (commercially available from Roche), ProClin150, ProClin300 (commercially available from Rohm & Haas), antibacterial (antifugal) agents such as benzalkonium chloride, KathonCG, p-hydroxymethylbenzoate, antibiotics such as amphotericin B, ampicillin, blasticidin S, chloramphenicol, dihydrostreptomycin, clindamycin, cycloheximide, filipin, G418, gentamycin, hygromycin, kanamycin, lincomycin, neomycin, polyoxin, penicillin, sulfamethizol, and tetracycline can be used. Examples of the surfactant include non-ionic surfactant, cationic surfactant, anionic surfactant and amphoteric surfactant. Specifically, non-ionic surfactants such as Adekanol 720N, B-795, B-797, LO-7, NP-690, NP-695, NP-720, PC-8, SO-120, SO-145, Brij 35, 98, 700, EMULGEN 109P, 430, 460, 707, 709, 810, 911, 935, 950, A-60,B66, n-dodecylmaltoside, Genapol X-080, MEGA-7, 8, 9, 10, NIKKOL BL-9EX, BL-20TX, HCD-100, MGO, MYO-6, MYL-10, NP-18TX, OP-10, TL-10, TMGO5, SL-10, octyl α-glucoside, octyl β-glucoside, octylthioglucoside, octylthiogalactoside, pentaethyleneglycol dodecylether, polyethylene ether W-1, Pluronic F-68, L-71, P-103, Nonidet P40, RHEODOL 460, TWL-103, TWL-106, saponin, sarcosinate PN, SPAN 20, 85, SM1080, sucrose monolaurate, Tetronic 704, Thesit, Triton X-100, X-114, X-305, Tween 20, 40, 80, cationic surfactants such as bis(hydroxymethyl)-(stearoylaminomethylcarbonyloxy) ethylamine chloride, benzyllaurylmethylsulfonium methylsulfate, 2-[(4-t-octylphenoxy)ethoxy] ethylmorpholine chloride, laurylpyridinium chloride, lauryl (tri-p-tolyl)phosphonium chloride, laurylphenylcyclotetramethylenephosphonium bromide, cetylpyridium chloride, cetyltrimethylammonium chloride, (polyoxyethylene) laurylamine, anionic surfactants such as sodium cholate, desoxycholic acid, N-lauroyl sarcosine, taurotaurocholic acid, and amphoteric surfactants such as CHAPS, CHAPSO, N,N-bis(octylaminoethyl)glycine, N-carboxymethyl-N-(stearyloxymethyl)pyridiumbetaine, N-palmitylsulfotaurin, lauryldimethylamine-oxide, and N-(laurylthioethoxy) methyl-N,N-dimethylbetaine can be used.

The reagent kit of the present invention can preserve each of the above-mentioned reagent component or two or more components in a single reagent. Therefore, the reagent kit of the present invention may be a single reagent composition containing all of the above-mentioned reagent components. However, when interfering components are present or a component that cannot be ensured stability under single preservation conditions is present, the constituent components are desirably divided and preserved.

The present invention also provides a reagent kit for creatinine or creatine determination, which contains, besides the above-mentioned reagent, creatine amidinohydrolase, sarcosine oxidase and, where necessary, creatinine amidohydrolase. The enzymes mentioned above can be used as appropriate.

The present invention further provides a reagent kit for homocysteine determination containing, besides the above-mentioned reagent, at least betaine, betaine-homocysteine methyltransferase and dimethylglycine oxidase. The enzymes mentioned above can be used as appropriate.

The present invention still yet provides a determination method of homocysteine, which method comprises bringing transferase utilizing homocysteine and other compound as a pair of substrates, and said other compound into contact with a sample, and measuring a compound produced by the reaction of the transferase without chromatography or antigen-antibody reaction.

The transferase to be used for the above-mentioned determination method may be, for example, an enzyme that transfers methyl to thiol of homocysteine. Preferably, it is betaine-homocysteine methyltransferase (EC 2.1.1.5), homocysteine methyltransferase (EC 2.1.1.10), and N5-methyltetrahydrofolate-homocysteine methyltransferase (EC 2.1.1.13), more preferably betaine-homocysteine methyltransferase.

The betaine-homocysteine methyltransferase (EC 2.1.1.5) to be used in the present invention produces dimethylglycine and methionine by reacting with homocysteine when betaine is a different substrate. For example, it can be obtained from mammal and microorganisms such as the genus *Pseudomonas*, and the genus Aspergillus.

When betaine-homocysteine methyltransferase is used, betaine is used as the other substrate, which is commercially available at a low cost in the form of hydrochloride.

The dimethylglycine, which is the product of the above-mentioned enzymatic reaction, can be measured by the following method.

Dimethylglycine is decomposed by dimethylglycine oxidase (EC 1.5.3.10) into sarcosine, formaldehyde and hydrogen peroxide according to the following formula: dimethylglycine+$H_2O$+$O_2 \rightarrow$ sarcosine+formaldehyde+$H_2O_2$ Therefore, by measuring the amount of oxygen consumed during the reaction or by measuring the production amount of hydrogen peroxide using a hydrogen peroxide sensor, or using a redox indicator directly and in the presence of peroxidase, dimethylglycine can be measured. Alternatively, produced formaldehyde can be indirectly measured by measuring absorbance in the UV region or visible region, or fluorescence using Hanz reagent, formaldehyde dehydrogenase, formaldehyde oxidase. For example, since reduced NAD (NADH) produced from NAD (nicotineamide adenine dinucleotide) by formaldehyde dehydrogenase reduces tetrazolium salt to give formazan pigment in the presence of an electron carrier such as diaphorase and methylphenazinium methylsulfate, the determination thereof affords quantitative measurement of homocysteine.

When sarcosine oxidase (EC 1.5.3.1) is further added, moreover, sarcosine is decomposed into glycine, formaldehyde and hydrogen peroxide, which affords sensitively higher measurement. Furthermore, measurement of production amount of hydrogen peroxide by reaction with formaldehyde oxidase affords improved sensitivity.

Dimethylglycine oxidase is an enzyme that acts on dimethylglycine produced by betaine-homocysteine methyltransferase to decompose into sarcosine, formaldehyde and hydrogen peroxide. For example, it can be obtained from a microorganism such as the genus Cylindrocarpon, the genus Achromobacter, and the genus *Arthrobacter*.

The sarcosine oxidase (EC 1.5.3.1) that acts on sarcosine produced by dimethylglycine oxidase to produce glycine, formaldehyde and hydrogen peroxide can be obtained from various animals, and a microorganism such as the genus *Arthrobacter*, the genus *Penicillium*), the genus *Bacillus*. Alternatively, a commercially available enzyme can be also used.

The above-mentioned enzyme may be one obtained by isolating a gene encoding each enzyme protein from a producing microorganism and allowing expression by genetic engineering. In addition, for example, one genetically modified to achieve improvement in enzymatic properties, such as specific activity and stability of the enzyme protein can be also used.

Hydrogen peroxide produced by dimethylglycine oxidase and/or sarcosine oxidase can be measured by direct measurement of absorbance in the UV region, calorimetric assay using catalase and titanium oxide reagent (*Agric. Biol. Chem.*, 38, 1213 (1974)), titration assay using potassium permanganate. For highly sensitive measurement, it is reacted with a hydrogen donor chromogenic reagent in the presence of peroxidase and, where necessary, reacted with a coupler such as 4-aminoantipyrine, 3-methyl-2-benzothiazolinone and the produced pigment is measured to preferably afford a quantitative measurement. The chromogenic reagent to be used is not particularly limited and various commercially available ones can be used. Examples thereof include N-ethyl-N-sulfopropyl-m-anisidine, N-ethyl-N-sulfopropyl-aniline, N-methyl-N-sulfopropyl-aniline, N-butyl-N-sulfopropyl-aniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-sulfopropyl-m-toluidine, N-ethyl-N-sulfopropyl-o-toluidine, N-ethyl-N-sulfopropyl-p-toluidine, N-ethyl-N-(2-hydroxy-3-sulfopropyl)-m-anisidine, N-ethyl-N-(2-hydroxy-3-sulfopropyl)aniline, N-ethyl-N-(2-hydroxy-3-sulfopropyl)-3,5-dimethoxyaniline, N-(2-hydroxy-3-sulfopropyl)-3,5-dimethoxyaniline, N-ethyl-N-(2-hydroxy-3-sulfopropyl)-3,5-dimethoxyaniline, N-ethyl-N-(2-hydroxy-3-sulfopropyl)-m-toluidine, N-sulfopropylaniline, p-chlorophenol, p-bromophenol, 2,4-dichlorophenol, p-hydroxybenzoate, 3,3',5,5'-tetramethylbenzidine, N-(3-sulfopropyl)3,3',5,5'-tetramethylbenzidine, and N,N,N',N',N'',N''-hexa(3-sulfopropyl)-4,4',4''-triaminotriphenylmethane. In addition, hydrogen peroxide can be measured directly or in the co-existence of a catalase by monitoring consumed oxygen with a sensor.

Sarcosine produced by dimethylglycine oxidase can be analyzed by analyzing formaldehyde or hydrogen peroxide produced by reacting with sarcosine oxidase by the aforementioned method, or by measuring a pigment produced by reacting sarcosine dehydrogenase in the presence of an electron carrier and color developing pigment. Examples of the electron carrier include diaphorase, methylphenazinium methylsulfate, methylene blue, and potassium ferricyanide. Examples of the pigment include tetrazolium salt, and indophenol. In addition, sarcosine dehydrogenase can be obtained directly from mammal, *Pseudomonas* microorganism, or from a recombinant prepared by isolating the gene of the enzyme and processing by genetic engineering.

Formaldehyde produced by dimethylglycine oxidase is preferably measured by reacting glutathione, glutathione-dependent formaldehyde dehydrogenase and oxidized coenzyme, and, where necessary, a reduced coenzyme of the kind different from the oxidized coenzyme with a sample and measuring the produced or consumed compound.

As the glutathione-dependent formaldehyde dehydrogenase, the aforementioned enzyme obtained in the present invention is most preferably used. Conventionally known enzymes derived from mammal, higher plant, methylotrophic yeast, and bacteria can be also used. For example, commercially available enzymes derived from Candida yeast can be used. Specific examples include FORMALDEHYDE DEHYDROGENASE (Sigma, Glutathione dependent).

This enzyme may be obtained by isolating a gene encoding the enzyme protein from a microorganism producing the same and allowing expression by genetic engineering, or include a mutant and chemically modified enzymes processed to have improved enzymatic properties of, for example, enzyme specific activity, and stability.

Examples of the coenzyme include nicotineamide adenine dinucleotide and its analogs (NADs), nicotineamide adenine dinucleotide phosphate and its analogs (NADPs), thionicotineamide adenine dinucleotide and its analogs (thio-NADs) or thionicotineamide adenine dinucleotide and its analogs (thio-NADPs), wherein NADs and NADPs may be those that can be used as coenzyme by glutathione-dependent formaldehyde dehydrogenase. Known examples include nicotineamide adenine dinucleotide, acetylpyridine adenine dinucleotide, and acetylpyridine adeninehypoxanthine dinucleotide, and nicotineamide hypoxanthine dinucleotide for NADs, and nicotineamide adenine dinucleotide phosphate, acetylpyridine adenine dinucleotide phosphate, acetylpyridine adeninehypoxanthine dinucleotide phosphate, and nicotineamide hypoxanthine dinucleotide phosphate for NADPs. As the thio-NADs or thio-NADPs, those that can be used as coenzyme by glutathione-dependent formaldehyde dehydrogenase may be used. Known examples include thionicotineamide adenine dinucleotide, thionicotineamide hypoxanthine dinucleotide, thionicotineamide adenine dinucleotide phosphate, and thionicotineamide hypoxanthine dinucleotide phosphate.

The determination method of formaldehyde when conventionally known glutathione-dependent formaldehyde dehydrogenase is used may be any from among the aforementioned methods for novel glutathione-dependent formaldehyde dehydrogenase of the present invention, except those via a cycling reaction.

When the sample to be measured in the present invention is a biological sample, particularly plasma or urine, the homocysteine to be contained is largely bonded with a circulating protein such as albumin, or in the state of a disulfide bond with cysteine or other homocysteine molecule. Therefore, for the determination of the total homocysteine, the sample needs to be treated with a reducing agent or enzymatic reaction in advance to allow production of free homocysteine.

The reducing agent to be used for this end may be, for example, thiols, borohydrides, amalgams, phosphine, and phosphothioate. Specifically, thiols may be dithiothreitol, dithioerythritol, 2-mercaptoethanol, 2-mercaptomethylamine, cysteine, cystamine, cysteine thioglycorate, thioglycolic acid, and reduced glutathione, borohydrides may be sodium borohydride, and amalgams may be sodium amalgam.

When the enzyme to be used in the present invention is subject to inhibition of activity by the thiol compound, the reagent may show degraded properties. However, dimethylglycine oxidase free of an influence of thiol compound has not been reported.

The present invention provides a novel dimethylglycine oxidase stable against thiol compound. Examples of such thiol compound include dithiothreitol, dithioerythritol, 2-mercaptoethanol, 2-mercaptoethanesulfonate, 2-mercaptoethylamine, cysteine, homocysteine, N-acetylcysteine, thioglycerol, thioglycolic acid, reduced glutathione and salts thereof. Preferably, the dimethylglycine oxidase in the presence of 0.05 mmol/L dithiothreitol retains at least 50% of the enzyme activity in the absence of dithiothreitol.

Preferably, the dimethylglycine oxidase of the present invention is an enzyme further having the following physico-chemical properties.

(a) action: acting on dimethylglycine in the presence of oxygen to produce sarcosine, formaldehyde and hydrogen peroxide, and b) Km value for dimethylglycine: not more than 15 mM.

The dimethylglycine oxidase of the present invention is not particularly limited as regards its derivation as long as it shows the above-mentioned properties. Preferably, it is derived from a microorganism belonging to the genus Arthrobacter, the genus *Streptomyces*, particularly preferably derived from *Arthrobacter nicotianae* strain IFO14234 or *Streptomyces* mutabilis strain IFO12800. The strains IFO14234 and IFO12800 are available from the Institute for Fermentation, Osaka (IFO) (17-85, Juso-honmachi, 2-chome, Yodogawa-ku, Osaka 532-8686 Japan).

The dimethylglycine oxidase of the present invention may be genetically modified to improve enzymatic activity, such as specific activity and stability, by randomly or site-specifically inducing mutation as long as resistance to the above-mentioned thiol compound can be retained.

The dimethylglycine oxidase of the present invention can be obtained by isolation and purification of a cell or tissue culture capable of producing the enzyme, or by isolating a gene encoding the enzyme protein by a conventional method and allowing expression thereof in a suitable host according to genetic recombination techniques. Preferable embodiment of the former is the following method Any of the above-mentioned dimethylglycine oxidase-producing microorganism, such as *Arthrobacter nicotianae* strain IFO14234 or *Streptomyces* mutabilis strain IFO12800, is cultured in a nutrient medium. The nutrient medium to be used may be a synthetic medium or a natural medium that contains carbon source, nitrogen source, mineral and other necessary nutrients in suitable amounts that the strain to be used can utilize. As the carbon source, for example, malic acid, and succinic acid can be used. As the nitrogen source, for example, nitrogen-containing natural products such as peptones, beef extract, and yeast extract, and inorganic nitrogen-containing compounds such as ammonium chloride, and ammonium citrate can be used. As the mineral, for example, potassium phosphate, sodium phosphate, and magnesium sulfate can be used.

The culture is generally shaking culture or aeration-agitation culture. The culture temperature is about 20–about 40° C., preferably about 25–about 37° C., and the culture pH is about 5–about 9, preferably controlled to about 6–about 8. As long as the strain in use can grow, other conditions may be employed. The culture period is generally about 1–about 7 days, dimethylglycine oxidase is generally produced and accumulated in the cell.

The dimethylglycine oxidase of the present invention can be purified by a purification method generally used. For example, after recovery of the cells, disruption by ultrasonication, mechanical disruption with glass beads, disruption with French Press, or lysis with surfactant are applied to extract intracellular fractions. The obtained extract is subjected to salting out with ammonium sulfate, sodium sulfate, metal aggregation with magnesium chloride, calcium chloride, aggregation with protamin, polyethyleneimine, ion-exchange chromatography with DEAE (diethylaminoethyl)-sepharose, or CM (carboxymethyl)-sepharose, to purify glutathione-dependent formaldehyde dehydrogenase.

The use of betaine-homocysteine methyltransferase, dimethylglycine oxidase of the present invention and glutathione-dependent formaldehyde dehydrogenase enables detection of a trace amount of homocysteine contained in a sample at a concentration of not more than 1 µmol/L.

Methionine which is the other product of the betaine-homocysteine methyltransferase reaction can be measured using a known method. For example, there are mentioned a method including direct measurement based on known calorimetric assay by nitroprusside reaction, ninhydrin reaction (e.g., *J. Biol. Chem.*, 176, 789 (1948)) and a method including measurement of ketoacid, ammonia and hydrogen peroxide produced by methionine rasemase, amino acid oxidase and methionine γ-lyase. The ketoacid can be measured by, for example, a colorimetric assay using reaction with 3-methyl-2-benzothiazolonehydrazone, ammonia can be measured by, for example, a calorimetric assay according to the indophenol method, fluorometric assay of a reaction product with o-futalaldehyde, and hydrogen peroxide can be measured by the above-mentioned method.

Methionine rasemase is known to be produced from bacteria belonging to the genus *Pseudomonas*, and the genus *Streptpcoccus*. As the amino acid oxidase, enzymes derived from mammal, bacteria belonging to the genus *Pseudomonas* are known. As one specifically acting on methionine, an amino acid oxidase contained in snake toxin is known. As the methionine γ-lyase, enzymes derived from the bacteria belonging to the genus *Pseudomonas*, and the genus *Clostridium* are known, from which methionine γ-lyase can be isolated and purified, or can be obtained from a recombinant prepared by isolating a gene encoding the enzyme protein and processing according to genetic recombination techniques.

It is known that the betaine-homocysteine methyltransferase can efficiently use dimethylthetin besides betaine, as a methyl donor to homocysteine (*J. Bacteriol.*, 113(1), 218 (1973)). Therefore, dimethylthetin may be added, instead of betaine, to the enzyme as a substrate other than homocysteine, and methionine thus produced is measured by any of the above-mentioned methods to measure homocysteine in the sample.

Homocysteine methyltransferase is an enzyme that catalyzes the following reactions.

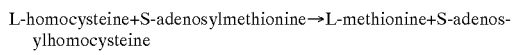

Therefore, by measuring the produced methionine according to the above-mentioned method, homocysteine can be measured.

Homocysteine methyltransferase can be harvested from mammal, plant, and yeast (*Saccharomyces*). It may be obtained by isolating a gene encoding the enzyme protein and allowing expression thereof in a suitable host according to genetic recombination techniques or may be genetically modified in properties by spontaneous or artificial mutation.

When homocysteine methyltransferase is used, S-adenosylmethionine is used as the other substrate, which is commercially available.

N5-Methyltetrahydrofolate-homocysteine methyltransferase is an enzyme that catalyzes the following reactions.

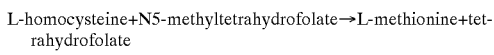

Therefore, by measuring the produced methionine according to the above-mentioned method, or by oxidizing tetrahydrofolate using NADP-dependent tetrahydrofolate dehydrogenase and measuring absorbance in the UV region or visible region, homocysteine can be measured.

N5-Methyltetrahydrofolate-homocysteine methyltransferase can be harvested from mammal or *E. coli*. In addition, NADP-dependent tetrahydrofolate dehydrogenase can be harvested from higher animal or plant. These enzymes may be obtained by isolating a gene encoding each enzyme and allowing expression thereof in a suitable host by genetic engineering or may be genetically modified in properties by spontaneous or artificial mutation.

When this enzyme is used, N5-methyltetrahydrofolate is used as the other substrate, which is commercially available.

The present invention also provides a reagent kit for use in the above-mentioned homocysteine determination method. The reagent kit for homocysteine determination of the present invention contains at least buffer, transferase utilizing homocysteine and other compound as a pair of substrates, said other compound and a reagent for measuring a compound produced by the reaction of the enzyme.

In a preferable embodiment, the reagent kit for homocysteine determination of the present invention contains buffer, betaine, betaine-homocysteine methyltransferase, dimethylglycine oxidase, and a reagent for analyzing at least one of formaldehyde, sarcosine or hydrogen peroxide produced by the reactions of the enzymes. Furthermore, it may contain sarcosine oxidase. As the betaine-homocysteine methyltransferase, dimethylglycine oxidase and sarcosine oxidase, those mentioned above are preferable, but are not particularly limited. The "reagent for analyzing at least one of formaldehyde, sarcosine or hydrogen peroxide produced by the reactions of the enzymes" may be those based on the aforementioned principle. The reagent for analyzing formaldehyde may be formaldehyde dehydrogenase, formaldehyde oxidase, Hanz reagent, CTA reagent (*J. Biol. Chem.*, 231, 813 (1958)), Purpald reagent (*Anal. Biochem.*, 234(1), 50 (1996)) or a reagent containing phenylhydrazine, potassium ferricyanide, chloroform and methanol in combination and the like. The reagent for analyzing hydrogen peroxide may be peroxidase, hydrogen donor chromogenic reagent and, where necessary, a coupler such as 4-aminoantipyrine, 3-methyl-2-benzothiazolinone, catalase, titanium oxide reagent, and potassium permanganate. The reagent for analyzing sarcosine may be sarcosine oxidase, the above-mentioned reagent for analyzing formaldehyde or hydrogen peroxide produced by the enzymatic reaction, sarcosine dehydrogenase, electron carrier, and color developing pigment.

In a particularly preferable embodiment, the reagent kit for homocysteine determination of the present invention can contain buffer, betaine, betaine-homocysteine methyltransferase, dimethylglycine oxidase, glutathione, glutathione-dependent formaldehyde dehydrogenase and an oxidized coenzyme that the glutathione-dependent formaldehyde dehydrogenase can use. Where necessary, it can further contain sarcosine oxidase. As the betaine-homocysteine methyltransferase, dimethylglycine oxidase, glutathione-dependent formaldehyde dehydrogenase and oxidized coenzyme, those mentioned above can be preferably used. As the glutathione-dependent formaldehyde dehydrogenase, when formaldehyde is measured using the enzyme newly obtained in the present invention, the reagent kit preferably contains a reduced coenzyme of the kind different from the above-mentioned oxidized coenzyme.

In a different embodiment, the reagent kit for homocysteine determination of the present invention contains buffer, betaine, betaine-homocysteine methyltransferase, dimethylglycine oxidase, and a reagent for measuring methionine produced by the reaction of the enzyme. The reagent for analyzing methionine may be those based on the aforementioned principle, such as nitroprusside reagent, ninhidrin reagent, methionine rasemase, amino acid oxidase, methionine γ-lyase, the above-mentioned ketoacid analysis reagent, the above-mentioned ammonia analysis reagent, and the above-mentioned hydrogen peroxide analysis reagent.

In another embodiment, the reagent kit for homocysteine determination of the present invention contains buffer, betaine-homocysteine methyltransferase, dimethylthetin, and a reagent for measuring a compound produced by the reaction of the enzyme. As the compound produced by the reaction of the enzyme, methionine is specifically exemplified. The reagents for analyzing methionine may be those mentioned above.

In another embodiment, the reagent kit for homocysteine determination of the present invention contains buffer, S-adenosylmethionine, homocysteine methyltransferase and a reagent for measuring a compound produced by the reaction of the enzyme. The compound produced by the reaction of the enzyme may be methionine. The reagents for analyzing methionine may be those mentioned above.

In a still another embodiment, the reagent kit for homocysteine determination of the present invention contains buffer, N5-methyltetrahydrofolate, N5-methyltetrahydrofolate-homocysteine methyltransferase and a reagent for measuring a compound produced by the reaction of the enzyme. As the compound produced by the reaction of the enzyme, methionine and tetrahydrofolate are mentioned. The reagents for analyzing methionine may be those mentioned above. The reagent for analyzing tetrahydrofolate may be NADP-dependent tetrahydrofolatedehydrogenase.

The present invention is explained in detail in the following by way of Examples. It is needless to say that the present invention is not limited by these Examples.

EXAMPLE 1

Preparation of Glutathione-Dependent Formaldehyde Dehydrogenase

The activity of the glutathione-dependent formaldehyde dehydrogenase of the present invention was measured under the following reagent and measurement conditions.
<Reagents>
reagent A 100 mM potassium phosphate buffer (pH 7.5)
reagent B 10 mM aqueous oxidized NAD solution
reagent C 20 mM aqueous formaldehyde solution
reagent D 20 mM aqueous glutathione solution <Measurement Conditions>
Reagent A, reagent B, reagent C and reagent D were mixed in ratios of 2.1 ml, 0.3 ml, 0.3 ml and 0.3 ml, respectively, to give a reagent mixture. This reagent mixture (3 ml) is preincubated at 37° C. for about 5 min and 0.1 ml of enzyme solution is admixed, which is followed by reaction at 37° C. for 4 min. Then, changes in absorbance at 340 nm per minute are measured. As a blind trial, distilled water is added to the reagent mixture instead of the enzyme solution and changes in absorbance are measured in the same manner. The amount of an enzyme that produces 1 μmole of hydrogen peroxide per 1 min under the above-mentioned conditions is taken as 1 unit (U).

One loopful of methylotrophic yeast Hansenula nonfermentans strain IFO1473 was inoculated to 60 ml YPD medium (1% D-glucose, 1% polypeptone, 1% yeast extract; pH 5.0), and after shaking culture at 30° C. for 24 hr, the strain was transferred to 6 L of glutathione-dependent formaldehyde dehydrogenase producing medium (2% methanol, 0.5% D-glucose, 1% polypeptone, 1.6% yeast extract, 0.2% hydrogendipotassium phosphate, 0.7% dihydrogenpotassium phosphate), and aeration-agitation cultured at 30° C. for 48 hours. After completion of the culture, the culture broth was centrifuged and the cells were suspended in 20 mM potassium phosphate buffer (pH 7.5). The cells were ruptured by glass beads and centrifuged to give a supernatant. The obtained enzyme solution was treated with polyethyleneimine to remove nucleic acid and separated and purified by ammonium sulfate fractionation, deionization by sephadex G-25, DEAE sepharose chromatography, phenylsepharose chromatography, hydroxyapatite chromatography and Superdex 200 gel filtration chromatography to give about 90 mg of a purified enzyme standard product. The standard product obtained by this method showed a single band on electrophoresis (SDS-PAGE), and the specific activity at this time was about 250 U/mg protein.

The enzyme activity of the glutathione-dependent formaldehyde dehydrogenase obtained by the above-mentioned method was measured under the same conditions as the above-mentioned activity measurement conditions except the use of oxidized thio-NAD instead of the oxidized NAD of reagent B. As a result, the reactivity of this enzyme with oxidized thio-NAD was 61% of the reactivity with oxidized NAD.

As a comparative example, the enzyme activity of commercially available glutathione-dependent formaldehyde dehydrogenase (Sigma, derived from Candida boidinii) was measured in the same manner. As a result, the reactivity of this enzyme with oxidized thio-NAD was 22% of the reactivity with oxidized NAD.

EXAMPLE 2

Preparation of Betaine-Homocysteine Methyltransferase

The activity of the betaine-homocysteine methyltransferase of the present invention was measured under the following reagent and measurement conditions.
<Reagents>
reagent A 50 mM potassium phosphate buffer (pH 7.5)
reagent B 100 mM DL-homocysteine solution (dissolved in reagent A)
reagent C 100 mM betaine (dissolved in reagent A)
reagent D 0.2% aqueous pentacyanoanmineiron(III) sodium solution
reagent E acetic acid
reagent F 10% aqueous sodium nitrite solution <Measurement Conditions>

Reagent B (0.075 ml) and reagent C (0.125 ml) are added to an enzyme solution (2.3 ml) and admixed, which is followed by reaction at 37° C. for 1 h. After the completion of the reaction, reagent D (5 ml) is added and the mixture is stirred. After standing for 1 min, 1 ml each of reagent E and reagent F were added in this order and the mixture is stirred. After standing for 30 min at room temperature, absorbance at 520 nm is measured. Using L-methionine dissolved in reagent A instead of the enzyme solution, absorbance is measured in the same manner and a standard curve is drawn, from which the amount of methionine produced by the enzymatic reaction is measured. The amount of an enzyme that produces 1 µmole of methionine per 1 h under the above-mentioned conditions is taken as 1 unit (U).

Two kinds of primers (SEQ ID NOs. 1 and 2) capable of amplifying a full length cDNA encoding betaine-homocysteine methyltransferase (*J. Biol. Chem.*, 271(37), 22831 (1998)) derived from human whose nucleotide sequence is known were prepared, and using them and human liver cDNA (Clontech) as a template, a DNA fragment encoding betaine-homocysteine methyltransferase derived from human was amplified by polymerase chain reaction (PCR). PCR was performed under the following reaction solution composition and reaction conditions.

<Reaction Solution Composition>
KODPlus DNA polymerase (TOYOBO) 1 Unit/50 µl
10× reaction buffer (attached to kit) 5 µl/50 µl
template cDNA 1.5 µg/50 µl
dATP, dTTP, dGTP, dCTP each 0.2 mM
primer each 25 µmols/50 µl
<Reaction Conditions; 30 Cycles in Total of the Following (2)–(4)>

|  |
|---|
| (1) 95° C., 2 min (denaturing) |
| (2) 95° C., 30 sec (denaturing) |
| (3) 60° C., 30 sec (annealing) |
| (4) 68° C., 1 min (elongation) |

After PCR reaction, a part of the reaction solution was subjected to agarose gel electrophoresis and an about 1.2 kbp amplified single band was confirmed. This amplified fragment was recovered using a DNA fragment purification kit (MagExtractor PCR&Gel Clean Up; TOYOBO) and was treated with Nde I and BamH I restriction enzymes. Then, pET11a plasmid (Stratagene) was treated with Nde I and BamH I restriction enzymes, and ligated with the above-mentioned DNA fragment using T4 DNA ligase (TOYOBO). Using this, Epicurian Coli BL21(DE3)-CodonPlusTM-RIL competent cell (Stratagene) was transformed, and plated on LB agar medium containing ampicillin (1% polypeptone, 0.5% yeast extract, 0.5% NaCl, 100 µg/ml ampicillin; pH 7.2) and cultured at 37° C. for 16 h.

The obtained colony was subjected to shaking culture in LB medium (60 ml) containing ampicillin at 30° C. for 16 h, and inoculated to 6 L of 2× YT medium supplemented with zinc chloride and ampicillin (1.6% polypeptone, 1% yeast extract, 0.5% NaCl, 34 µg/ml zinc chloride, 100 mg/ml ampicillin; pH 7.2) and subjected to aeration-agitation culture at 37° C. After about 2.5 h when absorbance at 600 nm of the culture broth reached about 1.0, isopropyl-β-D-thiogalactopyranoside was added to a concentration of 1 mM and the mixture was cultured for 4 more hours. After completion of the culture, the culture broth was centrifuged and the cells were suspended in 20 mM potassium phosphate buffer (pH 7.5) containing 5 mM 2-mercaptoethanol and 1 mM EDTA. The cells were ruptured in a French Press and centrifuged to give a supernatant. The obtained enzyme solution was treated with polyethyleneimine to remove nucleic acid, and separated and purified by deionization using sephadex G-25, DEAE sepharose chromatography, hydroxyapatite chromatography and Superdex 200 gel filtration chromatography to give about 50 mg of the purified enzyme standard product. The standard product obtained by this method showed a single band on electrophoresis (SDS-PAGE), and the specific activity at this time was about 2.1 U/mg protein.

EXAMPLE 3

Preparation of Dimethylglycine Oxidase

The activity of the dimethylglycine oxidase of the present invention was measured under the following reagent and measurement conditions.

<Reagents>
reagent A 100 mM dimethylglycine solution (dissolved in 100 mM potassium phosphate buffer (pH 7.5))
reagent B 0.1% aqueous 4-aminoantipyrine solution
reagent C 0.1% aqueous phenol solution
reagent D 25 U/ml aqueous peroxidase (TOYOBO; PEO-301) solution
<Measurement Conditions>

Reagent A, reagent B, reagent C and reagent D are mixed in ratios of 1.5 ml, 0.3 ml, 0.6 ml and 0.6 ml, respectively, to give a reagent mixture. This reagent mixture (3 ml) is preincubated at 37° C. for about 5 min and 0.1 ml of enzyme solution is admixed, which is followed by reaction at 37° C. for 4 min. Then, changes in absorbance at 500 nm per minute are measured. As a blind trial, distilled water is added to the reagent mixture instead of the enzyme solution and changes in absorbance are measured in the same manner. The amount of an enzyme that produces 1 µmole of hydrogen peroxide per 1 min under the above-mentioned conditions is taken as 1 unit (U).

(1) Isolation from *Arthrobacter nicotianae* Strain IFO14234

One loopful of *Arthrobacter nicotianae* strain IFO14234 was inoculated to 60 ml LB medium (1% polypeptone, 0.5% yeast extract, 0.5% NaCl; pH 7.2), and after shaking culture at 30° C. for 16 hr, the strain was transferred to 6 L of dimethylglycine oxidase producing medium (2% betaine, 1% polypeptone, 1.6% yeast extract, 1.4% hydrogendipotassium phosphate, 0.55% dihydrogenpotassium phosphate), and aeration-agitation cultured at 30° C. for 40 hours. After completion of the culture, the culture broth was centrifuged and the cells were suspended in 20 mM potassium phosphate buffer (pH 7.5). The cells were ruptured by glass beads and centrifuged to give a supernatant. The obtained enzyme solution was treated with polyethyleneimine to remove nucleic acid and separated and purified by ammonium sulfate fractionation, deionization by sephadex G-25, DEAE sepharose chromatography, phenylsepharose chromatography, and Superdex 200 gel filtration chromatography to give about 110 mg of a purified enzyme standard product. The standard product obtained by this method showed a single band on electrophoresis (SDS-PAGE), and the specific activity at this time was about 9.3 U/mg protein.

The enzyme activity of the dimethylglycine oxidase obtained by the above-mentioned method was measured under the same conditions as the above-mentioned activity measurement conditions except that 0.05 mmol/L dithiothreitol was used. As a result, the reactivity of this enzyme was 71% of the reactivity in the absence of dithiothreitol.

(2) Isolation from *Streptomyces mutabilis* Strain IFO12800

One loopful of *Streptomyces mutabilis* strain IFO12800 was inoculated to 60 ml dimethylglycine oxidase producing medium (2% betaine, 1% polypeptone, 1.6% yeast extract, 1.4% hydrogendipotassium phosphate, 0.55% dihydrogenpotassium phosphate), and after shaking culture at 30° C. for 72 hr, the culture broth was centrifuged and the cells were suspended in 20 mM potassium phosphate buffer (pH 7.5). The cells were ruptured by glass beads and centrifuged. The obtained extract was deionized by sephadex G-25.

With regard to the above-mentioned extract solution, the enzyme activity of dimethylglycine oxidase was measured under the same conditions as the above-mentioned activity measurement conditions except that 0.05 mmol/L dithiothreitol was used. As a result, the reactivity of this enzyme was 98% of the reactivity in the absence of dithiothreitol.

The Km values of the above-mentioned two kinds of dimethylglycine oxidases for dimethylglycine were measured. As a result, the Km value of the enzyme derived from *Arthrobacter nicotianae* strain IFO14234 was 13.6 mM, and that of the enzyme derived from *Streptomyces mutabilis* strain IFO12800 was 14.3 mM.

EXAMPLE 4

Measurement of Formaldehyde Standard Solution (1)

The activity of S-formylglutathione hydrolase to be used in this Example was measured according to the method described in *Biochimica. et Biophysica Acta*, 614, 81–91 (1980), and the enzyme activity of formate dehydrogenase was measured according to the method described in Eur. J. Biochem., 62(1), 151–160, Feb. 2, 1976.

The S-formylglutathione hydrolase to be used in this Example was obtained as follows.

One loopful of methylotrophic yeast (*Candida boidinii*) strain IFO1473 was inoculated to 60 ml YPD medium (1% D-glucose, 1% polypeptone, 1% yeast extract; pH 5.0), and after shaking culture at 30° C. for 24 hr, the strain was transferred to 6 L of S-formylglutathione hydrolase producing medium (2% methanol, 0.5% D-glucose, 1% polypeptone, 1.6%yeast extract, 0.2% hydrogendipotassium phosphate, 0.7% dihydrogenpotassium phosphate) and subjected to aeration-agitation culture at 30° C. for 48 hr. After completion of the culture, the culture broth was centrifuged and the cells were suspended in 20 mM potassium phosphate buffer (pH 7.5). The cells were ruptured by glass beads and centrifuged to give a supernatant. The obtained enzyme solution was treated with polyethyleneimine to remove nucleic acid, after which it was separated and purified by ammonium sulfate fractionation, deionization by sephadex G-25, DEAE sepharose chromatography, phenylsepharose chromatography, hydroxyapatite chromatography and Superdex 200 gel filtration chromatography to give about 10 mg of the purified enzyme standard product. The standard product obtained by this method showed almost a single band on electrophoresis (SDS-PAGE) and the specific activity at that time was about 900 U/mg protein.

Using various concentrations of aqueous formaldehyde solution (10 μL) as samples, the samples were mixed with 50 mM potassium phosphate buffer (300 μl, pH 7.5) containing 10 U/ml glutathione-dependent formaldehyde dehydrogenase (prepared in Example 1), 1 mM oxidized NAD, 3 mM glutathione, 5 U/ml S-formylglutathione hydrolase (prepared in the above) and 5 U/ml formate dehydrogenase (Sigma) and reacted at 37° C. for 10 min and absorbance at 340 nm was measured. As the blind trial, distilled water was added to the reagent mixture instead of the aqueous formaldehyde solution and changes in the absorbance were measured. The relationship between the absorbance upon termination of the reaction and formaldehyde concentration of the sample was as shown in Table 1 and FIG. 1, and the relationship was linear in the range of 0–500 μM of formaldehyde concentration, permitting quantitative measurement.

TABLE 1

| formaldehyde concentration (μmol/L) | Change in absorbance at 340 nm |
| --- | --- |
| 0 | 0 |
| 100 | 0.041 |
| 200 | 0.083 |
| 300 | 0.120 |
| 400 | 0.155 |
| 500 | 0.201 |

Note that this determination system is not a cycling method.

EXAMPLE 5

Measurement of Formaldehyde Standard Solution (2)

Using various concentrations of aqueous formaldehyde solution (10 μL) as samples, the samples were mixed with 50 mM HEPES buffer (300 μl, pH 8.0) containing 100 U/ml glutathione-dependent formaldehyde dehydrogenase (prepared in Example 1), 1 mM oxidized thionicotineamide adenine dinucleotide, 0.5 mM reduced nicotineamide adenine dinucleotide, 3 mM glutathione and 0.1% Triton X-100 and subjected to cycling reaction at 37° C. for 5 min, and absorbance at 405 nm was measured. As the blind trial, distilled water was added to the reagent mixture instead of the aqueous formaldehyde solution and changes in the absorbance were measured. The relationship between the increase in the absorbance at 1 min and 5 min after the start of the reaction and formaldehyde concentration of the sample was shown in Table 2 and FIG. 2, and the relationship was linear in the range of 0–50 μM of formaldehyde concentration, permitting quantitative measurement.

TABLE 2

| formaldehyde concentration (μmol/L) | Change in absorbance at 405 nm |
| --- | --- |
| 0 | 0 |
| 1 | 0.0017 |
| 2 | 0.0065 |
| 3 | 0.0091 |
| 5 | 0.0120 |
| 10 | 0.0247 |
| 15 | 0.0390 |
| 20 | 0.0494 |
| 30 | 0.0786 |
| 40 | 0.0986 |
| 50 | 0.120 |

Figure 2:
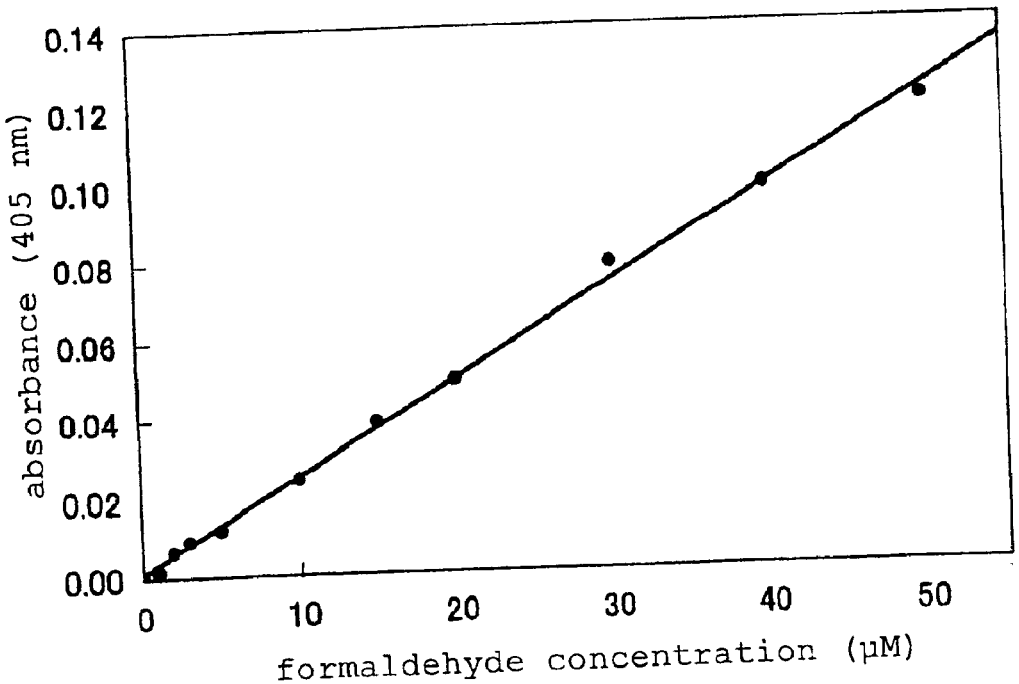
FIG. 2 shows the relationship between absorbance and formaldehyde concentration in Example 5.

From Table 2 and FIG. 2, it is clear that 1 μmol/L of formaldehyde could be measured by the cycling method.

EXAMPLE 6

Measurement of Creatinine Standard Solution

Using various concentrations of aqueous creatinine solution (5 μL) as samples, the samples were mixed with 50 mM HEPES buffer (200 μl, pH 8.0) containing 100 U/ml creatine amidohydrolase (TOYOBO; CNH-311), 50 U/ml creatine amidinohydrolase (TOYOBO; CRH-221), 10 U/ml TOYOBO; SAO-341) and 0.1% Triton X-100 and the mixture was reacted at 37° C. for 5 min. 50 mM HEPES buffer (100 μl, pH 8.0) containing 300 U/ml glutathione-dependent dehydrogenase (prepared in Example 1), 3 mM oxidized thionicotineamide adenine dinucleotide, 1.5 mM reduced nicotineamide adenine dinucleotide, 9 mM glutathione and 0.1% Triton X-100 was added and the mixture was subjected to cycling reaction at 37° C. for 5 min. The absorbance at 405 nm was measured. As the blind trial, distilled water was added to the reagent mixture instead of the aqueous formaldehyde solution and changes in the absorbance were measured. The relationship between the increase in the absorbance at 1 min and 5 min after the start of the reaction and creatinine concentration of the in Table 3 and FIG. 3, and the relationship was linear in the range of 0–100 μM of creatine concentration, permitting quantitative measurement.

TABLE 3

| creatinine concentration (μmol/L) | Change in absorbance at 405 nm |
|---|---|
| 0 | 0 |
| 10 | 0.011 |
| 20 | 0.023 |
| 40 | 0.042 |
| 60 | 0.066 |
| 80 | 0.084 |
| 100 | 0.113 |

Figure 3:
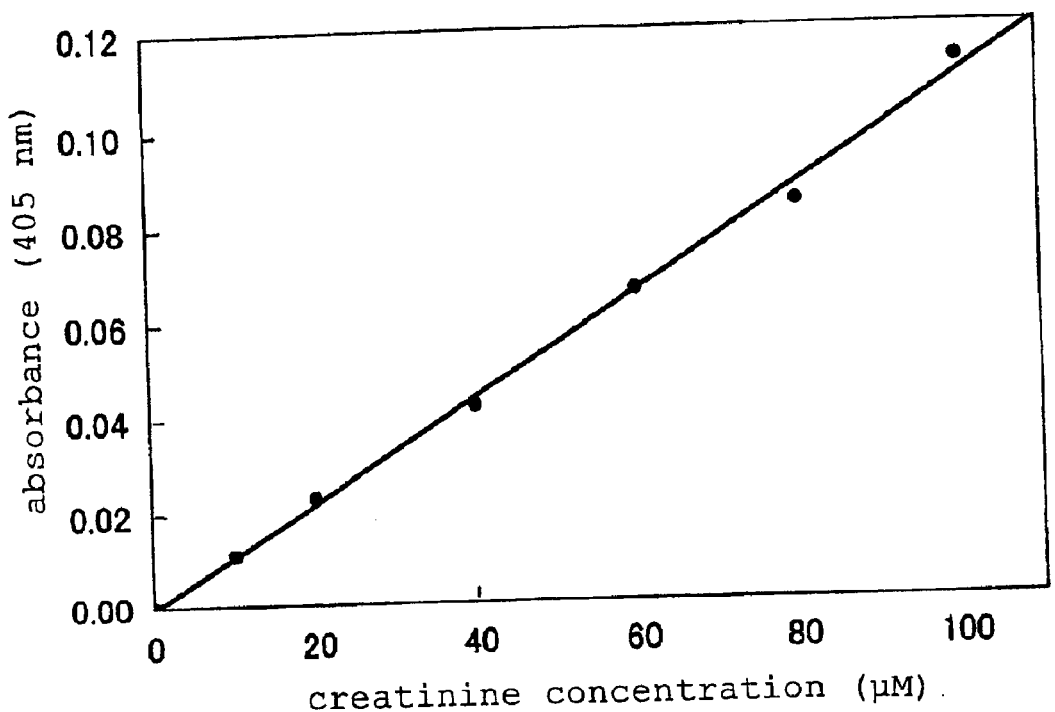
FIG. 3 shows the relationship between absorbance and creatinine concentration in Example 6.

From Table 3 and FIG. 3, it is clear that 10 μmol/L of creatinine could be measured by the cycling method.

EXAMPLE 7

Measurement of Homocysteine Standard Solution

As the betaine-homocysteine methyltransferase and dimethylglycine oxidase, those obtained in Example 2 and Examples 3(1) were used. The activity of betaine-homocysteine methyltransferase and dimethylglycine oxidase were measured in the same manner as in Example 2 and Example 3.

Various concentrations of aqueous L-homocystine solutions were incubated in 0.5 mM dithiothreitol at 37° C. for 30 min and the obtained L-homocysteine (10 μL) was used as a sample. The sample was mixed with 20 mM PIPES buffer (200 μl, pH 7.3) containing 20 mM betaine, 1 U/ml betaine-homocysteine methyltransferase, 7 U/ml dimethylglycine oxidase and 5 U/ml sarcosine oxidase (TOYOBO; SAO-341) and the mixture was reacted at 37° C. for 5 min. 50 mM HEPES buffer (100 μl, pH 8.2) containing 300 U/ml glutathione-dependent dehydrogenase (prepared in Example 1), 3 mM oxidized thionicotineamide adenine dinucleotide, 1.5 mM reduced nicotineamide adenine dinucleotide, 9 mM glutathione and 0.1% Triton X-100 was added and the mixture was subjected to cycling reaction at 37° C. for 5 min. The absorbance at 405 nm was measured. As the blind trial, 0.5 mM dithiothreitol was added to the reagent mixture instead of L-homocysteine solution and changes in the absorbance were measured. The relationship between the increase in the absorbance at 1 min and 5 min after the start of the reaction and homocysteine concentration of the sample was as shown in Table 4 and FIG. 4, and the relationship was linear in the range of 0–100 μM of homocysteine concentration, permitting quantitative measurement.

TABLE 4

| homocysteine concentration (μmol/L) | Change in absorbance at 405 nm |
|---|---|
| 0 | 0 |
| 1 | 0.0024 |
| 2 | 0.0062 |
| 3 | 0.0113 |
| 5 | 0.0226 |
| 10 | 0.0336 |
| 15 | 0.0589 |
| 20 | 0.0717 |
| 30 | 0.1092 |
| 40 | 0.1396 |
| 50 | 0.1720 |

Figure 4:
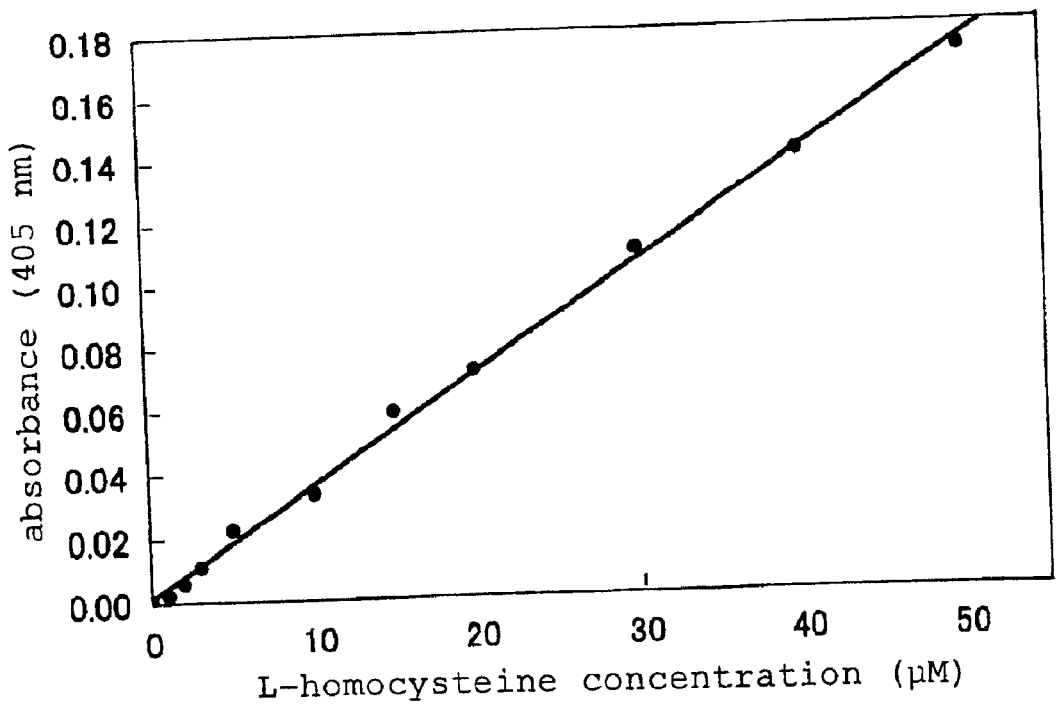
FIG. 4 shows the relationship between absorbance and homocysteine concentration in Example 7.

From Table 4 and FIG. 4, it is clear that 1 μmol/L of homocysteine could be measured by the cycling method.

This application is based on a patent application Nos. 2000-370445 and 2001-96724 filed in Japan, the contents of which are hereby incorporated by reference.

All of the references cited herein, including patents, patent applications and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for determining formaldehyde, which comprises bringing glutathione-dependent formaldehyde dehydrogenase having an optimal pH of about 7.5 to about 8.5 and having a ratio of reactivity with thio-NAD to reactivity with NAD of not less than 0.3, glutathione and an oxidized coenzyme into contact with a sample, and analyzing a compound resulting from the enzymatic reaction, wherein the gluathione-dependent formaldehyde dehydrogenase is derived from *Hansenula nonfermentans* IFO1473.

2. A method for determining formaldehyde, which comprises bringing glutathione-dependent formaldehyde dehydrogenase having a ratio of reactivity with thio-NAD to reactivity with NAD of not less than 0.3, glutathione, one compound selected from the group consisting of thio-NADs and thio-NADPs, and one compound selected from the group consisting of reduced NADs and reduced NADPs into contact with a sample to allow cycling reaction and analyzing changes in the amount of a compound due to the reaction.

3. A method for determining formaldehyde, which comprises bringing glutathione-dependent formaldehyde dehydrogenase having a ratio of reactivity with thio-NAD to reactivity with NAD of not less than 0.3, glutathione, one compound selected from the group consisting of reduced thio-NADs and reduced thio-NADPs , and one compound selected from the group consisting of NADs and NADPs into contact with a sample to allow cycling reaction and analyzing changes in the amount of a compound due to the reaction.

4. The method of claim 2, wherein the amount of the reduced thio-NADP or reduced thio-NAD compound is analyzed.

5. The method of claim 1, wherein a minimum detection limit of the formaldehyde is not more than 1 $\mu$mol/L.

6. The method of claim 2, wherein a minimum detection limit of the formaldehyde is not more than 1 $\mu$mol/L.

7. A method for determining a biological component that produces formaldehyde as a reaction intermediate, comprising measuring produced formaldehyde by the method of claim 1.

8. The method for determining a biological component that produces formaldehyde as a reaction intermediate, comprising measuring produced formaldehyde by the method of claim 2.

9. A method for determining homocysteine, which comprises bringing betaine, betaine-homocysteine methyltransferase, dimethylglycine oxidase and, where necessary, sarcosine oxidase into contact with a sample, and measuring, according to the method of claim 1, formaldehyde produced by the enzymatic reactions.

10. A method for determining homocysteine, which comprises bringing betaine, betaine-homocysteine methyltransferase, dimethylglycine oxidase and, where necessary, sarcosine oxidase into contact with a sample, and measuring, according to the method of claim 2, formaldehyde produced by the enzymatic reactions.

11. A method for determining creatine or creatinine, which comprises reacting creatine amidinohydrolase, sarcosine oxidase, and where necessary, creatinine amidohydrolase and measuring, according to the method of claim 1, formaldehyde produced by the enzymatic reactions.

12. A method for determining creatine or creatinine, which comprises reacting creatine amidinohydrolase, sarcosine oxidase, and where necessary, creatinine amidohydrolase and measuring, according to the method of claim 2, formaldehyde produced by the enzymatic reactions.

13. A method for determining homocysteine, which comprises bringing a transferase utilizing homocysteine and another compound as a pair of substrates and said another compound into contact with a sample and measuring the resulting compound and wherein said transferase and said another compound is a combination selected from the group consisting of betaine-homocysteine methyltransferase and betaine, betaine-homocysteine methyltransferase and dimethylthetin, homocysteine methyltransferase and S-adenosylmethionine, and N5-methyltetrahydrofolate-homocysteine methyltransferase and N5-methyltetrahydrofolate, and the resulting compound is methionine, and wherein the betaine, betaine-homocysteine methyltransferase, dimethylglycine oxidase and, where necessary, sarcosine oxidase are brought into contact with a sample, hydrogen peroxide produced by the enzymatic reactions is reacted with hydrogen donor chromogenic reagent and, where necessary, coupler, in the presence of peroxidase, and the resulting pigment is measured.

14. The method of claim 13, wherein the dimethylglycine oxidase is an enzyme stable to a thiol compound.

15. The method of claim 14, wherein the thiol compound is at least one kind selected from the group consisting of dithiothreitol, dithioerythritol, 2-mercaptoethanol, 2-mercaptoethanesulfonate, 2-mercaptoethylamine, cysteine, homocysteine, N-acetylcysteine, thiogylcerol, thioglycolic acid, reduced glutathione and salts thereof.

16. The method of claim 14, wherein the thiol compound is dithiothreitol.

17. The method of claim 14, wherein the dimethylglycine oxidase shows an enzyme activity in the presence of 0.05 mmol/L dithiothreitol of at least 50% of the enzyme activity in the absence of dithiothreitol.

18. The method of claim 14, wherein the dimethylglycine oxidase is an enzyme having the following physico-chemical properties: action: acting on dimethylglycine in the presence of oxygen to produce sarcosine, formaldehyde and hydrogen peroxide, and Km value for dimethylglycine: not more than 15 mM.

19. The method claim 14, wherein the dimethylglycine oxidase is derived from a microorganism.

20. The method of claim 19, wherein the dimethylglycine oxidase is derived from a microorganism belonging to the genus *Arthrobacter* or the genus *Streptomyces*.

21. The method of claim 20, wherein the dimethylglycine oxidase is derived from *Arthrobacter nicotianae* IFO14234 or *Streptomyces mutabilis* IFO12800.

22. The method of claim 13, wherein the betaine, betaine-homocysteine methyltransferase, dimethylglycine oxidase and, where necessary, sarcosine oxidase are brought in contact with a sample, formaldehyde produced by the enzymatic reactions is reacted with glutathione, glutathione-dependent formaldehyde dehydrogenase and oxidized coenzyme and the resulting reduced coenzyme is measured.

23. The method of claim 22, wherein the dimethylglycine oxidase is an enzyme stable to a thiol compound.

24. The method of claim 23, wherein the thiol compound is at least one kind selected from the group consisting of dithiothreitol, dithioerythritol, 2-mercaptoethanol, 2-mercaptoethanesulfonate, 2-mercaptoethylamine, cysteine, homocysteine, N-acetylcysteine, thiogylcerol, thioglycolic acid, reduced glutathione and salts thereof.

25. The method of claim 23, wherein the thiol compound is dithiothreitol.

26. The method of claim 23, wherein the dimethylglycine oxidase shows an enzyme activity in the presence of 0.05 mmol/L dithiothreitol of at least 50% of the enzyme activity in the absence of dithiothreitol.

27. The method of claim 23, wherein the dimethylglycine oxidase is an enzyme having the following physico-chemical properties: action: acting on dimethylglycine in the presence of oxygen to produce sarcosine, formaldehyde and hydrogen peroxide, and Km value for dimethylglycine: not more than 15 mM.

28. The method of claim 23, wherein the dimethylglycine oxidase is derived from a microorganism.

29. The method of claim 28, wherein the dimethylglycine oxidase is derived from a microorganism belonging to the genus *Arthrobacter* or the genus *Streptomyces*.

30. The method of claim 29, wherein the dimethylglycine oxidase is derived from *Arthrobacter nicotianae* IFO14234 or *Streptomyces mutabilis* IFO12800.

31. The method of claim 13, wherein the betaine, betaine-homocysteine methyltransferase, dimethylglycine oxidase and, where necessary, sarcosine oxidase are brought in contact with a sample, formaldehyde produced by the enzymatic reactions is reacted with glutathione, glutathione-dependent formaldehyde dehydrogenase and oxidized coenzyme and the resulting reduced coenzyme is measured.

32. The method of claim 31, wherein the dimethylglycine oxidase is an enzyme stable to a thiol compound.

33. The method of claim 32, wherein the thiol compound is at least one kind selected from the group consisting of dithiothreitol, dithioerythritol, 2-mercaptoethanol, 2-mercaptoethanesulfonate, 2-mercaptoethylamine, cysteine, homocysteine, N-acetylcysteine, thiogylcerol, thioglycolic acid, reduced glutathione and salts thereof.

34. The method of claim 32, wherein the thiol compound is dithiothreitol.

35. The method of claim 32, wherein the dimethylglycine oxidase shows an enzyme activity in the presence of 0.05 mmol/L dithiothreitol of at least 50% of the enzyme activity in the absence of dithiothreitol.

36. The method of claim 32, wherein the dimethylglycine oxidase is an enzyme having the following physico-chemical properties: action: acting on dimethylglycine in the presence of oxygen to produce sarcosine, formaldehyde and hydrogen peroxide, and Km value for dimethylglycine: not more than 15 mM.

37. The method of claim 32, wherein the dimethylglycine oxidase is derived from a microorganism.

38. The method of claim 37, wherein the dimethylglycine oxidase is derived from a microorganism belonging to the genus *Arthrobacter* or the genus *Streptomyces*.

39. The method of claim 38, wherein the dimethylglycine oxidase is derived from *Arthrobacter nicotianae* IFO 14234 or *Streptomyces mutabilis* IFO12800.

40. The method of claim 32, wherein a minimum detection limit of the homocysteine is not more than 1 $\mu$mol/L.

41. An isolated glutathione-dependent formaldehyde dehydrogenase (EC 1.2.1.2) having the following physico-chemical properties: action: acting on formaldehyde in the presence of one coenzyme selected from the group consisting of NADs, NADPs, thio-NADs and thio-NADPs, reduced glutathione to produce S-formylglutathione, a reduced coenzyme, a ratio of reactivity with thio-NAD to reactivity with NAD: not less than 0.3, optimal pH: about 7.5–about 8.5, pH stability: about 6.0–about 9.0, and heat stability: about 40° C. or less.

42. The glutathione-dependent formaldehyde dehydrogenase of claim 41, which is derived from a microorganism.

43. The glutathione-dependent formaldehyde dehydrogenase of claim 42, which is derived from methylotrophic yeast.

44. The glutathione-dependent formaldehyde dehydrogenase of claim 43, which is derived from *Hansenula* yeast.

45. The glutathione-dependent formaldehyde dehydrogenase of claim 44, which is derived from *Hansenula nonfermentans* IFO14234.

46. An isolated dimethylglycine oxidase (EC 1.5.3.10) having the following physico-chemical properties: action: acting on dimethylglycine in the presence of oxygen to produce sarcosine, formaldehyde and hydrogen peroxide, an enzyme activity in the presence of 0.05 mmol/L dithiothreitol of at least 50% of the enzyme activity in the absence of dithiothreitol, and Km value for dimethylglycine: not more than 15 mM.

47. The dimethylglycine oxidase of claim 46, which is derived from a microorganism.

48. The dimethylglycine oxidase of claim 47, which is derived from a microorganism belonging to the genus *Arthrobacter* or the genus *Streptomyces*.

49. The dimethylglycine oxidase of claim 48, which is derived from *Arthrobacter nicotianae* IFO14234, or *Streptomyces mutabilis* IFO12800.

50. A reagent kit for formaldehyde determination, which comprises at least buffer, glutathione, glutathione-dependent formaldehyde dehydrogenase having a ratio of reactivity with thio-NAD to reactivity with NAD of not less than 0.3 and a reagent for analyzing a compound produced by the enzymatic reaction.

51. The reagent kit for formaldehyde determination of claim 50, wherein the glutathione-dependent formaldehyde dehydrogenase has the following physico-chemical properties: action: production of S-formylglutathione and reduced coenzyme by action on formaldehyde in the presence of one oxidized coenzyme selected from the group consisting of NADs, NADPs, thio-NADs and thio-NADPs and reduced glutathione; optimal pH: about 7.5–about 8.5; pH stability: about 6.0–about 9.0; and heat stability: about 40° C. or less.

52. A reagent kit for formaldehyde determination, which comprises at least a buffer, glutathionde, glutathionde-dependent formaldehyde dehydrogenase having a ratio of reactivity with thio-NAD to reactivity with NAD of not less than 0.3, one compound selected from the group consisting of thio-NADs and thio-NADPs, and one compound selected from the group consisting of reduced NADs and reduced NADPs.

53. The reagent kit for formaldehyde determination of claim 52, wherein the glutathione-dependent formaldehyde dehydrogenase has the following physico-chemical properties: action: production of S-formylglutathione and reduced coenzyme by action on formaldehyde in the presence of one oxidized coenzyme selected from the group consisting of NADs, NADPs, thio-NADs and thio-NADPs and reduced glutathione; optimal pH: about 7.5–about 8.5; pH stability: about 6.0–about 9.0; and heat stability: about 40° C. or less.

54. A reagent kit for formaldehyde determination, which comprises at least a buffer, glutathionde, glutathione-dependent formaldehyde dehydrogenase having a ratio of reactivity with thio-NAD to reactivity with NAD of not less than 0.3, one compound selected from the group consisting of reduced thio-NADs and reduced thio-NADPs, and one compound selected from the group consisting of NADs and NADPs.

55. The reagent kit for formaldehyde determination of claim 54, wherein the glutathione-dependent formaldehyde dehydrogenase has the following physico-chemical properties: action: production of S-formylglutathione and reduced coenzyme by action on formaldehyde in the presence of one oxidized coenzyme selected from the group consisting of NADs, NADPs, thio-NADs and thio-NADPs and reduced glutathione; optimal pH: about 7.5- to about 8.5; pH stability: about 6.0- to about 9.0; and heat stability: about 40° C. or less.

56. A reagent kit for homocysteine determination, which comprises, in addition to the reagent of claim 50, betaine, betaine-homocysteine methyltransferase, dimethylglycine oxidase and, where necessary, sarcosine oxidase.

57. A reagent kit for homocysteine determination, which comprises, in addition to the reagent of claim 52, betaine, betaine-homocysteine methyltransferase, dimethylglycine oxidase and, where necessary, sarcosine oxidase.

58. A reagent kit for homocysteine determination, which comprises, in addition to the reagent of claim 54, betaine, betaine-homocysteine methyltransferase, dimethylglycine oxidase and, where necessary, sarcosine oxidase.

59. A reagent kit for creatinine or creatine determination, which comprises, in addition to the reagent of claim 50, creatine amidohydrolase, sarcosine oxidase and, where necessary, creatinine amidohydrolase.

60. A reagent kit for creatinine or creatine determination, which comprises, in addition to the reagent of claim 52, creatine amidohydrolase, sarcosine oxidase and, where necessary, creatinine amidohydrolase.

61. A reagent kit for creatine or creatine determination, which comprises, in addition to the reagent of claim 54, creatine amidohydrolase, sarcosine oxidase and, where necessary, creatinine amidohydrolase.

62. A reagent kit for homocysteine determination, which comprises at least a buffer, transferase utilizing homocysteine and another compound as a pair of substrates and a reagent for analyzing a compound produced by a reaction of the transferease utilizing homocysteine and said another compound as the substrates.

63. The reagent kit for homocysteine determination of claim 62, wherein the transferase and said other compound are a combination selected from the group consisting of betaine-homocysteine methyltransferase and betaine, betaine-homocysteine methyltransferase and dimethylthetin, homocysteine methyltransferase and S-adenosylmethionine and N5-methyltetrahydrofolate-homocysteine methyltransferase and N5-methyltetrahydrofolate, and the produced compound is methionine.

64. A reagent kit for homocysteine determination, which comprises a buffer, betaine, betaine-homocysteine methyltransferase, dimethylglycine oxidase and a reagent for measuring hydrogen peroxide produced by the enzymatic reactions.

65. The reagent kit of claim 64, wherein the reagent for measuring hydrogen peroxide comprises peroxidase, and a hydrogen donor chromogenic reagent.

66. The reagent for of claim 64, wherein the dimethylglycine oxidase has the following physico-chemical properties: action: acting on dimethylglycine in the presence of oxygen to produce sarcosine, formaldehyde and hydrogen peroxide, an enzyme activity is retained at least by 50% in the presence of 0.05 mmol/L dithiothreitol relative to the enzyme activity in the absence of dithiothreitol, and Km value for dimethylglycine: not more than 15 mM.

67. A reagent kit for homocysteine determination, which comprises betaine, betine-homocysteine methyltransferase, dimethlyglycine, oxidase and a reagent for determination of formaldehyde produced by the enzymatic reactions.

68. The reagent kit of claim 67, which comprises formaldehyde dehydrogenase and oxidized coenzyme as reagents for determination of the formaldehyde.

69. The reagent kit of claim 67, which comprises glutathione, glutathione-dependent formaldehyde dehydrogenase and oxidized coenzyme as reagents for determination of the formaldehyde.

70. The reagent kit of claim 67, wherein the dimethylglycine oxidase has the following physico-chemical properties: action: acting on dimethylglycine in the presence of oxygen to produce sarcosine, formaldehyde and hydrogen peroxide; enzyme activity: an enzyme activity in the presence of 0.05 mmol/L dithiothreitol of at least 50% of the enzyme activity in the absence of dithiothreitol; and Km value for dimethylglycine: not more than 15 mM.

71. The reagent kit of claim 64, further comprising sarcosine oxidase.

72. The reagent kit of claim 64, further comprising a coupler.

73. The reagent kit of claim 67, further comprising sarcosine oxidase.

* * * * *

UNITED STATES PATENT AND TRADEMARK OFFICE
CERTIFICATE OF CORRECTION

PATENT NO. : 6,867,012 B2
DATED : March 15, 2005
INVENTOR(S) : Kishimoto et al.

It is certified that error appears in the above-identified patent and that said Letters Patent is hereby corrected as shown below:

Column 1,
Line 14, change "homocysteine and" to -- homocysteine, --;

Column 2,
Line 49, change "depths vein thrombosis" to -- deep-vein thrombosis --;
Line 67, change "desulfrase" to -- desulfurase --;

Column 3,
Line 12, change "228998 A)" to -- 228998 A). --;
Line 28, change "ulfrase" to -- ulfurase --;
Line 50, change "creatine," to -- creatine --;

Column 13,
Line 12, change "Wen" to -- When --;

Column 14,
Lines 22 and 31, change "antifugal" to -- antifungal --;

Column 18,
Line 4, change "thioglycorate" to -- thioglycolate --;

Column 19,
Line 31, change "rasemase" to -- racemase --;
Line 39, change "rasemase" to -- rasemase --;
Line 41, change "*Streptpcoccus*" to -- *Streptococcus* --;

Column 20,
Line 55, delete "and the like";

Column 23,
Line 50, change "Epicurian Coli" to -- *Escherichia coli* --;

Column 27,
Line 46, change "L-homocystine" to -- L-homocysteine --;

Column 32,
Line 66, change "glutathionde, glutathionde-" to -- glutathione, glutathione --;

UNITED STATES PATENT AND TRADEMARK OFFICE
CERTIFICATE OF CORRECTION

PATENT NO. : 6,867,012 B2
DATED : March 15, 2005
INVENTOR(S) : Kishimoto et al.

It is certified that error appears in the above-identified patent and that said Letters Patent is hereby corrected as shown below:

Column 33,
Line 16, change "glutathionde" to -- glutathione --;

Column 34,
Line 3, "transferease" to -- transferase --; and
Line 32, change "betine-homocysteine" to -- betaine-homocysteine --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO.    : 6,867,012 B2
DATED         : March 15, 2005
INVENTOR(S)   : Kishimoto et al.

It is certified that error appears in the above-identified patent and that said Letters Patent is hereby corrected as shown below:

Column 1,
Line 14, change "homocysteine and" to -- homocysteine, --;

Column 2,
Line 49, change "depths vein thrombosis" to -- deep-vein thrombosis --;
Line 67, change "desulfrase" to -- desulfurase --;

Column 3,
Line 12, change "228998 A)" to -- 228998 A). --;
Line 28, change "ulfrase" to -- ulfurase --;
Line 50, change "creatine," to -- creatine --;

Column 13,
Line 12, change "Wen" to -- When --;

Column 14,
Lines 22 and 31, change "antifugal" to -- antifungal --;

Column 18,
Line 4, change "thioglycorate" to -- thioglycolate --;

Column 19,
Line 31, change "rasemase" to -- racemase --;
Line 39, change "rasemase" to -- rasemase --;
Line 41, change "*Streptpcoccus*" to -- *Streptococcus* --;

Column 20,
Line 55, delete "and the like";

Column 23,
Line 50, change "Epicurian Coli" to -- *Escherichia coli* --;

Column 27,
Line 46, change "L-homocystine" to -- L-homocysteine --;

Column 32,
Line 66, change "glutathionde, glutathionde-" to -- glutathione, glutathione- --;

Column 33,
Line 16, change "glutathionde" to -- glutathione --;

UNITED STATES PATENT AND TRADEMARK OFFICE
CERTIFICATE OF CORRECTION

PATENT NO. : 6,867,012 B2
DATED : March 15, 2005
INVENTOR(S) : Kishimoto et al.

It is certified that error appears in the above-identified patent and that said Letters Patent is hereby corrected as shown below:

Column 34,
Line 3, change "transferease" to -- transferase --; and
Line 32, change "betine-homocysteine" to -- betaine-homocysteine -- .

Signed and Sealed this

Twenty-eighth Day of February, 2006

JON W. DUDAS
*Director of the United States Patent and Trademark Office*